US011253347B2

(12) United States Patent
Haupt et al.

(10) Patent No.: US 11,253,347 B2
(45) Date of Patent: Feb. 22, 2022

(54) HEAD-ONLY AND/OR WHOLE BODY INHALATION EXPOSURE CHAMBER

(71) Applicants: The Government of the United States, as Represented by the Secretary of the Army, Fort Detrick, MD (US); Government of the United States of America, as represented by the Secretary of the Commerce, Gaithersburg, MD (US)

(72) Inventors: Brett R. Haupt, Thurmont, MD (US); Matthew E. Staymates, Damascus, MD (US); Larry E. Bowen, Williamsport, MD (US); Mark M. Bailey, Gaithersburg, MD (US); Jaime B. Anderson, Hagerstown, MD (US)

(73) Assignees: The Government of the United States, as represented by the Secretary of the Army, Fort Detrick, MD (US); Government of the United States of America, as represented by the Secretary of the Commerce, Gaithersburg, MD (US)

( * ) Notice: Subject to any disclaimer, the term of this patent is extended or adjusted under 35 U.S.C. 154(b) by 391 days.

(21) Appl. No.: 16/076,040

(22) PCT Filed: Feb. 7, 2017

(86) PCT No.: PCT/US2017/016811
§ 371 (c)(1),
(2) Date: Aug. 7, 2018

(87) PCT Pub. No.: WO2017/136855
PCT Pub. Date: Aug. 10, 2017

(65) Prior Publication Data
US 2020/0022795 A1    Jan. 23, 2020

Related U.S. Application Data

(60) Provisional application No. 62/292,355, filed on Feb. 7, 2016, provisional application No. 62/375,168, filed on Aug. 15, 2016.

(51) Int. Cl.
*A61D 7/04* (2006.01)
*A61M 15/00* (2006.01)

(52) U.S. Cl.
CPC ............ *A61D 7/04* (2013.01); *A61M 15/009* (2013.01); *A61M 15/0065* (2013.01);
(Continued)

(58) Field of Classification Search
CPC ....... A61D 7/04; A61D 7/00; A61M 15/0065; A61M 15/0086; A61M 15/009;
(Continued)

(56) References Cited

U.S. PATENT DOCUMENTS 3,367,308 A * 2/1968 Quattrone .............. A01K 1/031
119/420
3,863,914 A * 2/1975 O'Connor ......... A61M 16/0048
482/13
(Continued)

FOREIGN PATENT DOCUMENTS

CN    104305997 A    1/2015
DE    40 09 067 A1   12/1991
(Continued)

OTHER PUBLICATIONS

Broughton et al., "Effect of Electronic Compensation of Plethysmographic Airway Resistance Measurements," Pediatric Pulmonology, Vo. 42, Jul. 20, 2007, pp. 764-772.
(Continued)

*Primary Examiner* — Colin W Stuart
*Assistant Examiner* — Douglas Y Sul
(74) *Attorney, Agent, or Firm* — Leigh Callander

(57) ABSTRACT

A system for conducting inhalation studies includes an inhalation exposure chamber and an aerosol delivery line connected to the inhalation exposure chamber. The aerosol delivery line is configured to produce a bi-directional and symmetrical presentation of aerosol to the inhalation exposure chamber. A laminar flow element is configured to create an ante-chamber where complete and turbulent mixing of the aerosol occurs. A radial exhaust and the laminar flow element enable laminar flow of the aerosol through the inhalation exposure chamber.

20 Claims, 18 Drawing Sheets

(52) U.S. Cl.
CPC ..... *A61M 15/0086* (2013.01); *A61M 2205/50* (2013.01); *A61M 2206/11* (2013.01); *A61M 2206/16* (2013.01); *A61M 2250/00* (2013.01)

(58) Field of Classification Search
CPC .......... A61M 2205/50; A61M 2206/11; A61M 2206/16; A61M 2250/00; A61M 2209/02; A61M 2205/7518; A61M 2230/40; A61M 16/009; A61M 16/0627; A61M 2205/3393; A61M 2205/7509; A61M 2205/7545; A61M 11/001; A61M 11/00; A61M 11/06; A61M 13/00; A61B 5/091; A61G 10/00; A01K 1/00; A01K 1/06; A01K 13/003; B08B 15/00; B08B 15/002; B08B 15/007; B08B 15/02; B08B 15/023
USPC .......... 119/420; 128/202.12; 454/49, 56, 61, 454/62; 237/14
See application file for complete search history.

(56) References Cited

U.S. PATENT DOCUMENTS

| | | | |
|---|---|---|---|
| 4,348,985 A | 9/1982 | Leong | |
| 4,402,315 A | 9/1983 | Tsuda et al. | |
| 4,520,808 A | 6/1985 | LaBauve | |
| 4,710,887 A | 12/1987 | Ho | |
| 4,721,060 A | 1/1988 | Cannon et al. | |
| 4,781,146 A | 11/1988 | Spengler | |
| 4,860,741 A | 8/1989 | Bernstein et al. | |
| 5,025,619 A | 6/1991 | Cannon | |
| 5,109,797 A | 5/1992 | Briant et al. | |
| 5,124,029 A * | 6/1992 | Fjallstrom | B01D 33/15 209/250 |
| 5,124,133 A * | 6/1992 | Schoenrock | B01D 15/08 210/286 |
| 5,156,776 A | 10/1992 | Loedding et al. | |
| 5,255,668 A * | 10/1993 | Umeda | A61B 1/0055 600/139 |
| 5,297,502 A | 3/1994 | Jaeger | |
| 5,320,108 A | 6/1994 | Cloutier | |
| 5,379,777 A | 1/1995 | Lomask | |
| 5,487,378 A | 1/1996 | Robertson et al. | |
| 5,865,144 A * | 2/1999 | Semenuk | A01K 1/031 119/456 |
| 5,887,586 A | 3/1999 | Dahlback et al. | |
| 5,896,829 A | 4/1999 | Rothenberg et al. | |
| 6,016,803 A | 1/2000 | Volberg et al. | |
| 6,131,571 A | 10/2000 | Lampotang et al. | |
| 6,224,560 B1 | 5/2001 | Gazula et al. | |
| 6,725,859 B1 | 4/2004 | Rothenberg et al. | |
| 6,902,532 B2 * | 6/2005 | Lomask | A61B 5/0806 128/200.14 |
| 6,904,912 B2 | 6/2005 | Roy et al. | |
| 7,377,276 B2 | 5/2008 | Roy et al. | |
| 7,527,021 B2 | 5/2009 | Mead et al. | |
| 8,029,342 B2 * | 10/2011 | Anderson | A61D 7/04 452/66 |
| 8,221,329 B2 | 7/2012 | Hartings et al. | |
| 8,985,100 B2 | 3/2015 | Minocchieri et al. | |
| 9,180,263 B2 | 11/2015 | Gumaste et al. | |
| 2002/0103443 A1 * | 8/2002 | Roy | A61D 7/04 600/532 |
| 2003/0125633 A1 * | 7/2003 | Hartings | A61D 7/04 600/532 |
| 2004/0030304 A1 * | 2/2004 | Hunt | A61L 15/26 604/317 |
| 2004/0095746 A1 * | 5/2004 | Murphy | F21V 23/04 362/86 |
| 2004/0216737 A1 | 11/2004 | Anderson et al. | |
| 2007/0028918 A1 * | 2/2007 | Tsuyuki | A61D 7/04 128/203.12 |
| 2007/0175475 A1 * | 8/2007 | Grauke | A61G 10/026 128/205.26 |
| 2007/0186868 A1 * | 8/2007 | Dietrich | A22B 3/00 119/678 |
| 2008/0306437 A1 * | 12/2008 | Jacobson | A61M 5/142 604/67 |
| 2009/0013997 A1 | 1/2009 | Barnewall et al. | |
| 2009/0211534 A1 * | 8/2009 | Schenkel | A61D 7/04 119/420 |
| 2011/0000482 A1 * | 1/2011 | Gumaste | A61D 7/04 128/200.23 |
| 2011/0023789 A1 * | 2/2011 | Delagrammatikas | A61D 7/04 119/420 |
| 2014/0020687 A1 | 1/2014 | Cullen et al. | |
| 2014/0245964 A1 * | 9/2014 | Stevens | A61M 16/18 119/420 |
| 2016/0007815 A1 * | 1/2016 | Esposito | A47L 9/02 15/393 |
| 2016/0030695 A1 * | 2/2016 | Chang | A61M 16/06 128/205.25 |
| 2016/0101269 A1 * | 4/2016 | Benz | A61B 17/135 606/202 |
| 2016/0151591 A1 * | 6/2016 | Le Bars | A61D 7/04 128/202.22 |
| 2017/0135311 A1 * | 5/2017 | Driver | A61D 7/00 |

FOREIGN PATENT DOCUMENTS

| | | |
|---|---|---|
| JP | 2-177955 A | 7/1990 |
| WO | 96/00046 A1 | 1/1996 |
| WO | 96/13294 A1 | 5/1996 |
| WO | 02/060336 A1 | 8/2002 |
| WO | 03/101339 A1 | 12/2003 |
| WO | 2004/071330 A2 | 8/2004 |

OTHER PUBLICATIONS

Decker et al., abstract for "A Method for Measuring Respiratory Volume Parameters of Large Animals During Exposure to Aerosols," American Industrial Hygiene Association Journal, vol. 40, No. 7, 1979, printed from www.tandfonline.com/doi/abs/10.1080/15298667991430000 on Nov. 30, 2015.

Hartings et al., "The Automated Bioaersol Exposure System: Preclinical Platform Development and a Respiratory Dosimetry Application With Nonhuman Primates," Journal of Pharmacological and Toxicological Methods, vol. 49, 2004, pp. 39-55.

Espacenet, English Abstract of CN104305997.
Espacenet, English Abstract of DE4009067.
Espacenet, English Abstract of JP02177955.

* cited by examiner

FIG. 13

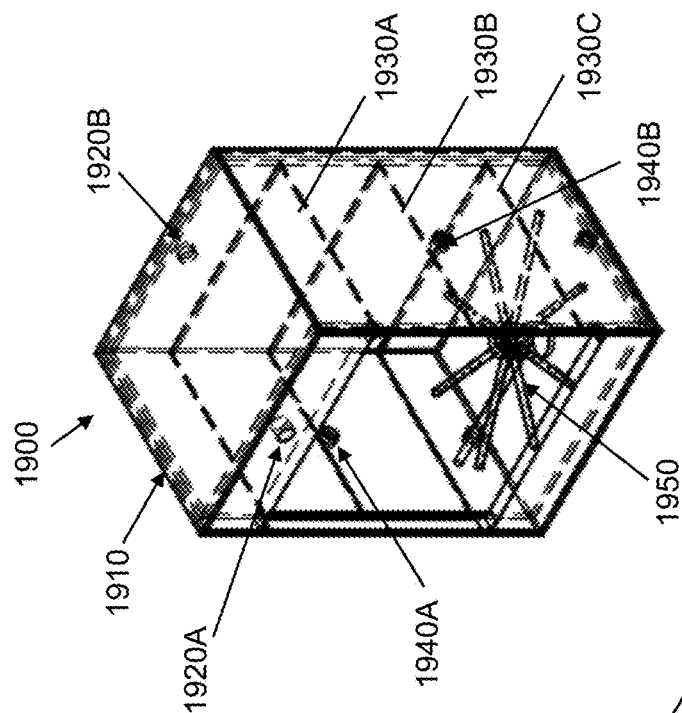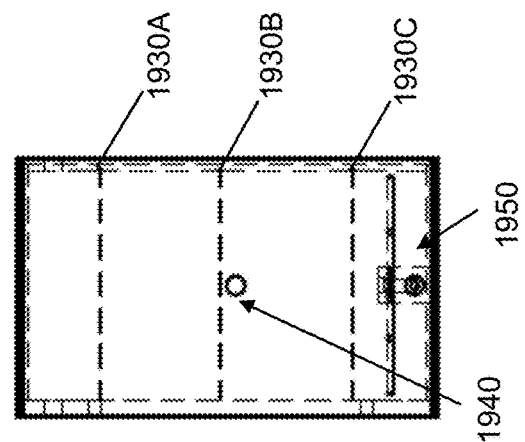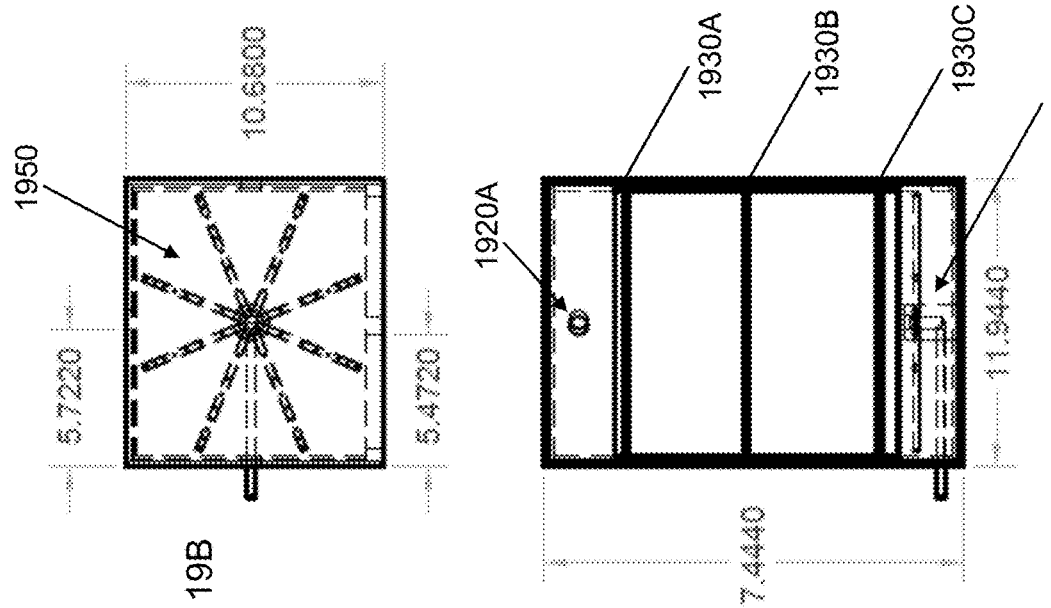

```
┌─────────────────────────────────────────────────────┐
│ Detect positive pressure pulses and negative        │──── 2010
│ pressure pulses in an exposure chamber              │
└─────────────────────────────────────────────────────┘
                         │
                         ▼
┌─────────────────────────────────────────────────────┐
│ Determine tidal volume and frequency based on       │──── 2020
│ the detected positive and negative pressure pulses  │
└─────────────────────────────────────────────────────┘
                         │
                         ▼
┌─────────────────────────────────────────────────────┐
│ Calculate a respiratory minute volume as a          │──── 2030
│ product of the tidal volume and the frequency       │
└─────────────────────────────────────────────────────┘
                         │
                         ▼
┌─────────────────────────────────────────────────────┐
│ Calculate a cumulative inspired volume as a product │──── 2040
│ of the respiratory minute volume and an exposure duration │
└─────────────────────────────────────────────────────┘
                         │
                         ▼
┌─────────────────────────────────────────────────────────┐
│ Calculate the desired inhaled volume of aerosol with the │──── 2050
│ cumulative inspired volume and the theoretical aerosol concentration │
└─────────────────────────────────────────────────────────┘
```

FIG. 20

HEAD-ONLY AND/OR WHOLE BODY INHALATION EXPOSURE CHAMBER

This application is the national stage application of PCT international application no. PCT/US2017/016811, filed on Feb. 7, 2017, which claims the benefit of U.S. Patent Application Ser. No. 62/292,355 filed on 7 Feb. 2016 with the U. S. Patent and Trademark Office, which is hereby incorporated by reference.

This invention was made with support from the United States Department of the Army. The United States Government has certain rights in this invention.

I. FIELD OF THE INVENTION

The present invention relates to a head-only inhalation exposure chamber for use on nonhuman primates. The present invention also relates to a whole body inhalation exposure system.

II. BACKGROUND OF THE INVENTION

Nonhuman primates (NHPs) are frequently challenged with infectious aerosols by head-only inhalation. In traditional head-only inhalation systems, a sedated NHP is positioned in a supine orientation and its head is inserted inside a rectangular chamber. The head is supported on a wire grid and a flexible piece of dental dam material is sealed around the animal's neck and between the animal's neck and the chamber. Aerosol is directed into the top of the chamber, flows past the animal's head, and is exhausted out of the bottom of the chamber. In examining this traditional method, testing with visible aerosols revealed that the unidirectional presentation of the aerosol resulted in persistent turbulent flow patterns throughout the chamber. Additionally, the asymmetrical exhaust manifold contributed to an abbreviated T99 and an increased dead space.

The current art utilizes a unidirectional, asymmetrical aerosol delivery line and symmetrical exhaust line that result in an acutely short observed T99 (time to 99% equilibrium concentration) and a large amount of turbulent flow and dead space in the chamber. An observed T99 that is less than the theoretical T99 is indicative of plug flow (short circuiting) in the chamber. The dead space percentage is an indication of unequal distribution (non-homogeneity) of aerosol in the chamber.

The various embodiments of this invention resolve several design weaknesses of the current art in head-only exposure chambers adversely affecting chamber operational efficiency.

III. SUMMARY OF THE INVENTION

Embodiments of the invention include a head-only chamber comprising an opposed normal aerosol delivery line, a laminar flow element and a radial exhaust. The opposed normal delivery line produces a bidirectional and symmetrical presentation of aerosol to the chamber. The laminar flow element creates an antechamber where complete, turbulent mixing occurs. The laminar flow element and radial exhaust enable laminar flow of the aerosol through the chamber and past the test system's head. Improvements in chamber operational efficiency have been confirmed using video and pictures of a dense aerosol in the chamber, by calculation of T99 and determination of the aerosol temporal stability in the chamber.

At least one embodiment provides a system having an inhalation exposure chamber. The inhalation exposure chamber can include four sidewalls, where one of the sidewalls includes an aperture dimensioned to receive a primate head therethrough. The system can include four cages in the inhalation exposure chamber. An aerosol delivery line can be connected to the inhalation exposure chamber, where the aerosol delivery line is configured to produce a bidirectional and symmetrical presentation of aerosol to the inhalation exposure chamber. The aerosol delivery line can be centrally located at the top of the inhalation exposure chamber. The aerosol delivery line can be a 12.0 inch long pipe having a 1.5 inch diameter. The aerosol delivery line can include two 0.25 inch wide by 8.0 inch long slots positioned 180° apart.

In at least one embodiment, the system includes a laminar flow element configured to create an antechamber where complete and turbulent mixing of the aerosol occurs, where the laminar flow element is located below the aerosol delivery line. The laminar flow element can include a sheet having a plurality of perforations. For example, the laminar flow element includes an 8.0 inch×8.0 inch×0.735 inch honeycomb. In another example, the laminar flow element includes an 8.0 inch×8.0 inch×0.0156 inch sheet with 0.25 inch perforations. In yet another example, the laminar flow element includes an 8.0 inch×8.0 inch×0.0625 inch sheet with 0.0625 inch diameter perforations. The system can include at least one additional laminar flow element including a sheet having a plurality of perforations.

The system can include a radial exhaust, where the radial exhaust and the laminar flow element can enable laminar flow of the aerosol through the inhalation exposure chamber. The radial exhaust can be centrally located at the bottom of the inhalation exposure chamber. The radial exhaust can include eight tubes positioned radially around a central hub, where each tube can include a sealed distal end and a plurality of lateral holes. The radial exhaust can include four first tubes having a first length and four second tubes having a second length, where the second length is greater than the first length. The radial exhaust can include 0.375 inch diameter tubes positioned radially around a 1.5 inch diameter×2.0 inch high central hub. Each of the tubes can include a sealed distal end and five 0.125 inch lateral apertures. The system can include one or more sample collection ports located at a midpoint of a wall of the inhalation exposure chamber.

Given the following enabling descriptions of the drawings, the invention should be evident to one ordinarily skilled in the art.

IV. BRIEF DESCRIPTION OF THE DRAWINGS

FIG. 13 is a schematic diagram of an embodiment of the novel head-only chamber test system.

FIG. 19A is a top perspective view of an inhalation exposure chamber system according to another embodiment of the invention. FIG. 19B is a top view of the inhalation exposure chamber system illustrated in FIG. 19A. FIG. 19C is a side view of the inhalation exposure chamber system illustrated in FIG. 19A. FIG. 19D is a side cross-sectional view of the inhalation exposure chamber system illustrated in FIG. 19A.

FIG. 20 is a flow diagram illustrating a method for controlling aerosol respiratory exposure according to an embodiment of the invention.

Figure 21:
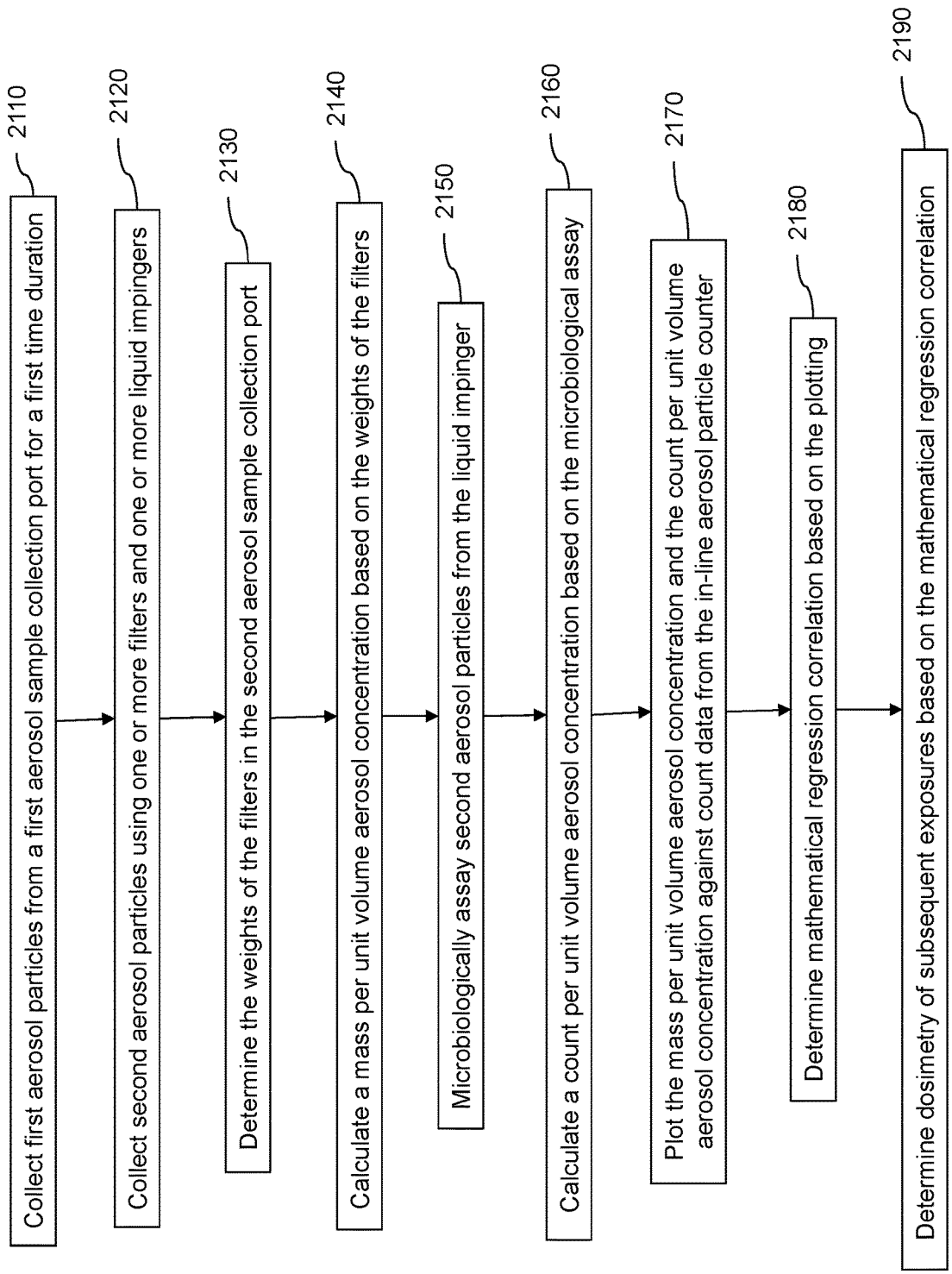

FIG. 21 is a flow diagram illustrating a method for controlling aerosol respiratory exposure according to an embodiment of the invention.

Figure 22:
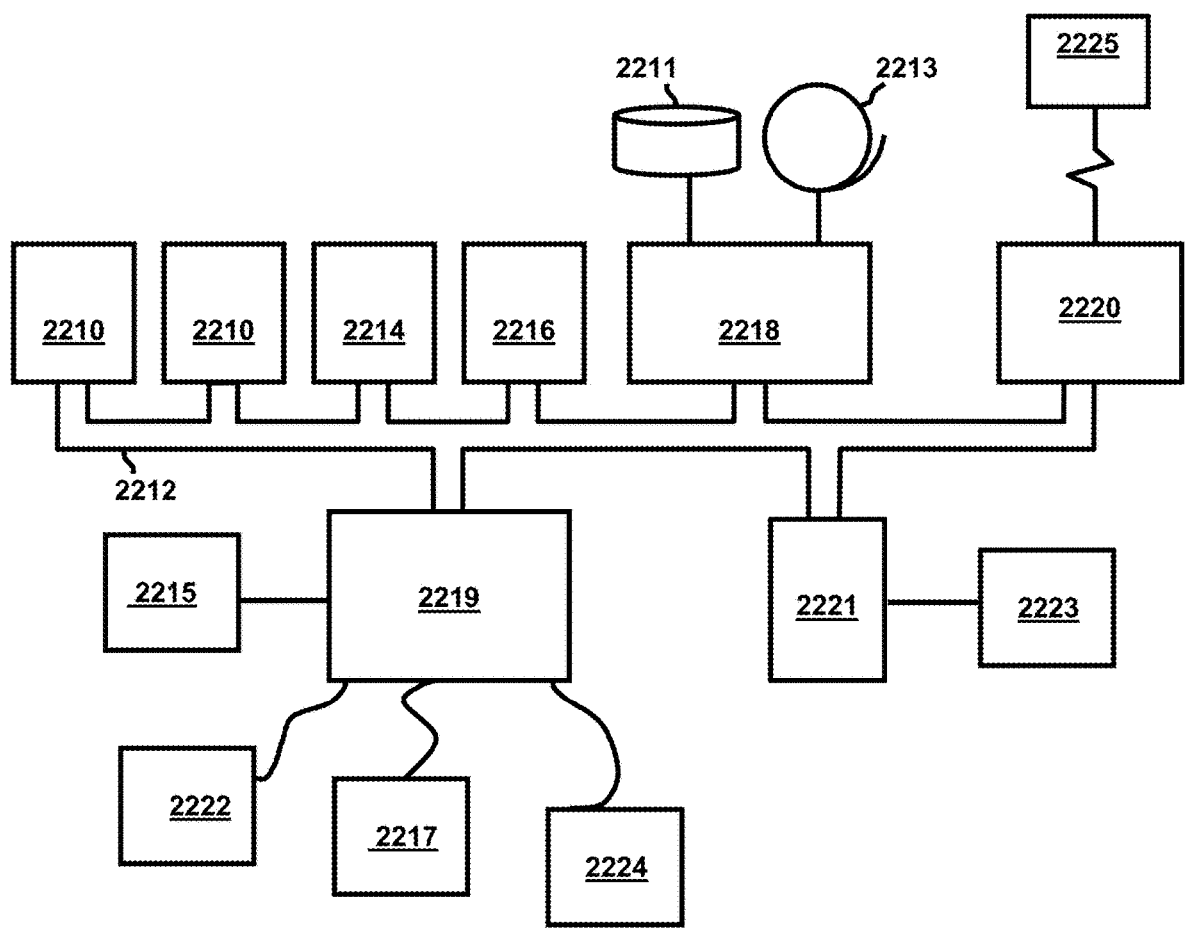

FIG. 22 illustrates a computer program product and computer implementation according to an embodiment of the invention.

Figure 23:
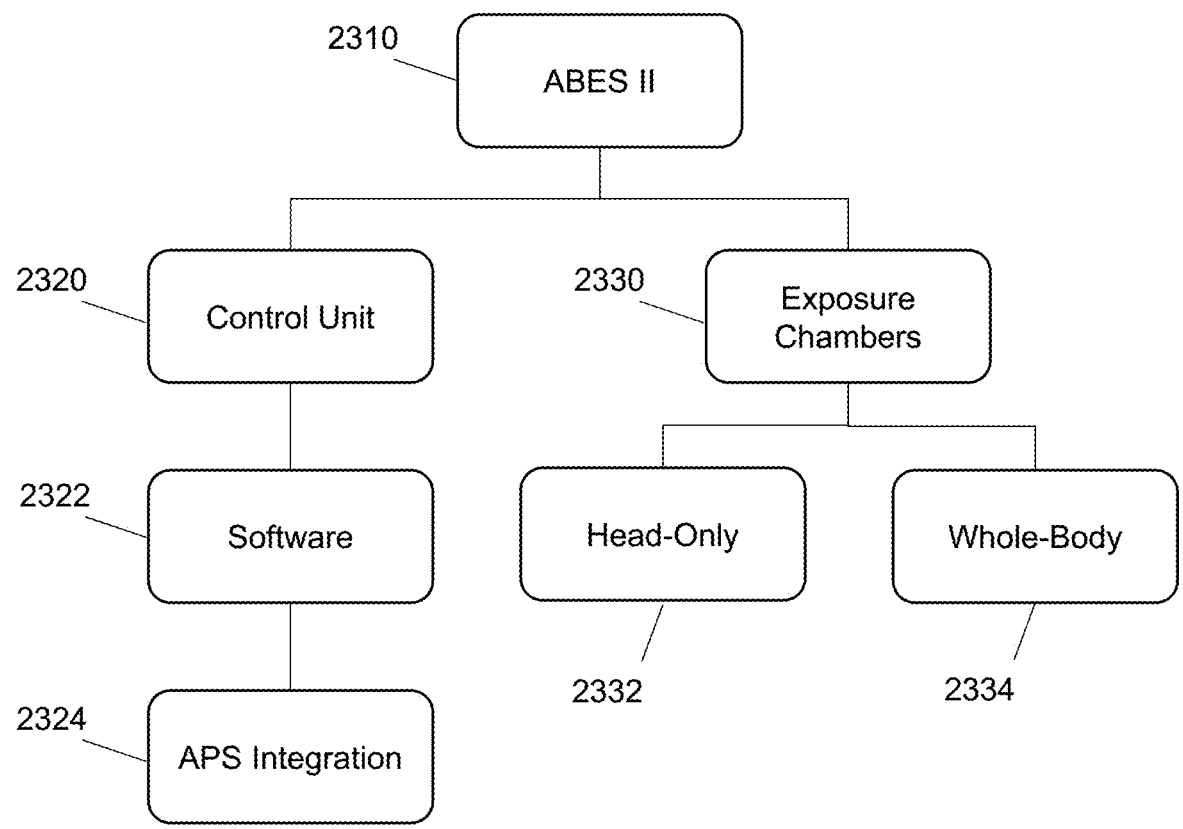

FIG. 23 illustrates a schematic of one embodiment of the computer system of this invention.

Figure 24:
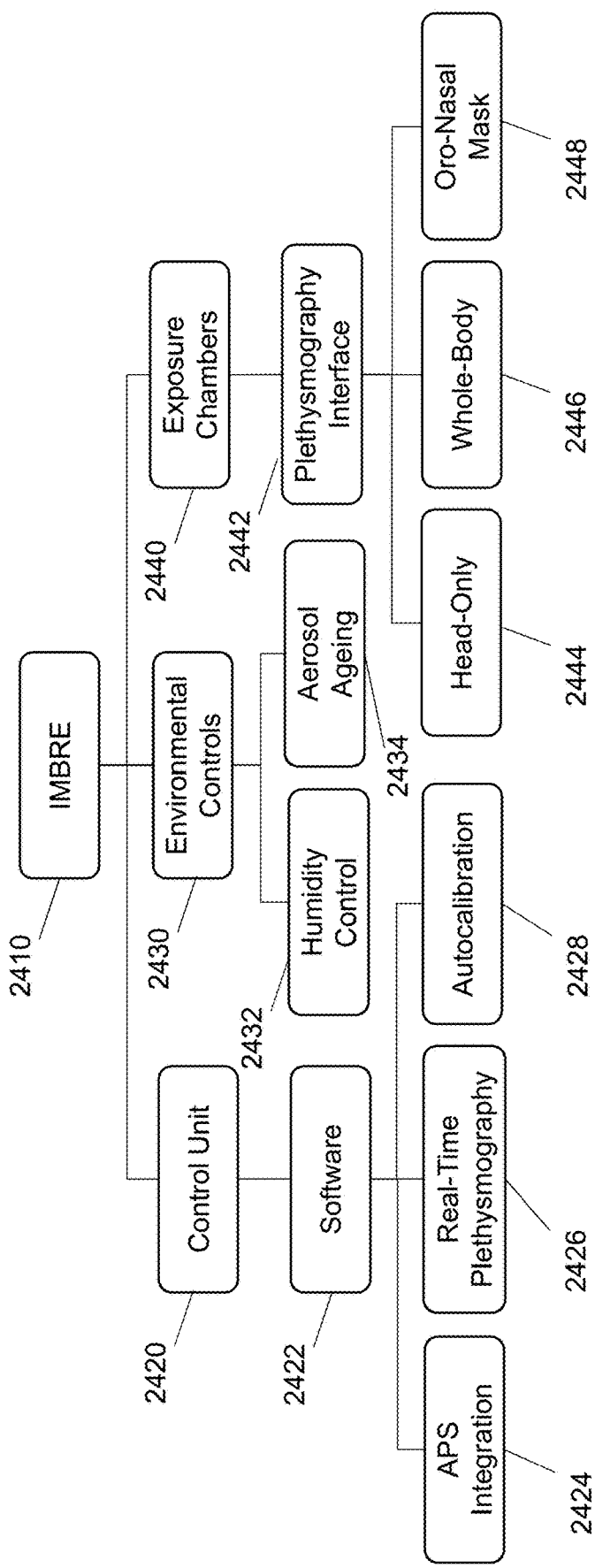

FIG. 24 illustrates a schematic of one embodiment of the computer system of this invention.

V. DETAILED DESCRIPTION OF THE DRAWINGS

In order to provide a clear and consistent understanding of the specification and claims, including the scope to be given such terms, the following definitions are provided.

As used herein, "communication means" refers to means for conveying digital information, synchronously and asynchronously, as an electromagnetic signal from one electronic device to another, to include without limitation: Universal Serial Bus (USB) ports, FIREWIRE™, wired technology, optical fiber, wireless (including BLUETOOTH™, ANT+ TM), analog-to-digital conversion (e.g. through a microphone), cellular, microwave, satellite, infrared, Large Area Networks, Local Area Networks, Internet/Web, and radio.

The term "data-entry means" refers to any device for accepting data from a subject, to include without limitation: keyboards, keypads, touchpads, tactile sensors, capacitive sensing devices, and conductance sensing devices, regardless of whether the data entry means requires the use of a stylus or similar writing implements.

The term "statistical methods" refers to both descriptive and inferential statistics well known in the art, to include without limitation those statistical methods, tests (parametric and non-parametric) and procedures particular to the fields of biostatistics and psychological statistics.

The term "storage means" refers to any means for storing data that is accessible by an electronic digital computer to include, without limitation: volatile memory (RAM, SRAM, DRAM, Z-RAM, TTRAM, A-RAM and ETA RAM) and non-volatile memory (ROM, flash memory, magnetic computer storage devices and optical discs), whether or not the data is stored in a database.

As used herein, the term "subject" means any living organism, including humans, and mammals.

As will be appreciated by one skilled in the art based on this disclosure, aspects of the present invention may be embodied as a system, method or computer program product. Accordingly, aspects of the present invention may take the form of an entirely hardware embodiment, a processor operating with software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this disclosure, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Computer program code for carrying out operations for aspects of the present invention may be written in any combination of one or more programming languages, including an object oriented programming language such as Java, Smalltalk, C++, C#, Transact-SQL, XML, or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute with the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

For purposes of clarity of disclosure, and not by way of limitation, the detailed description of the invention is described by way of the demonstrative examples discussed below, and as further described in FIGS. 1-24.

Figure 1:
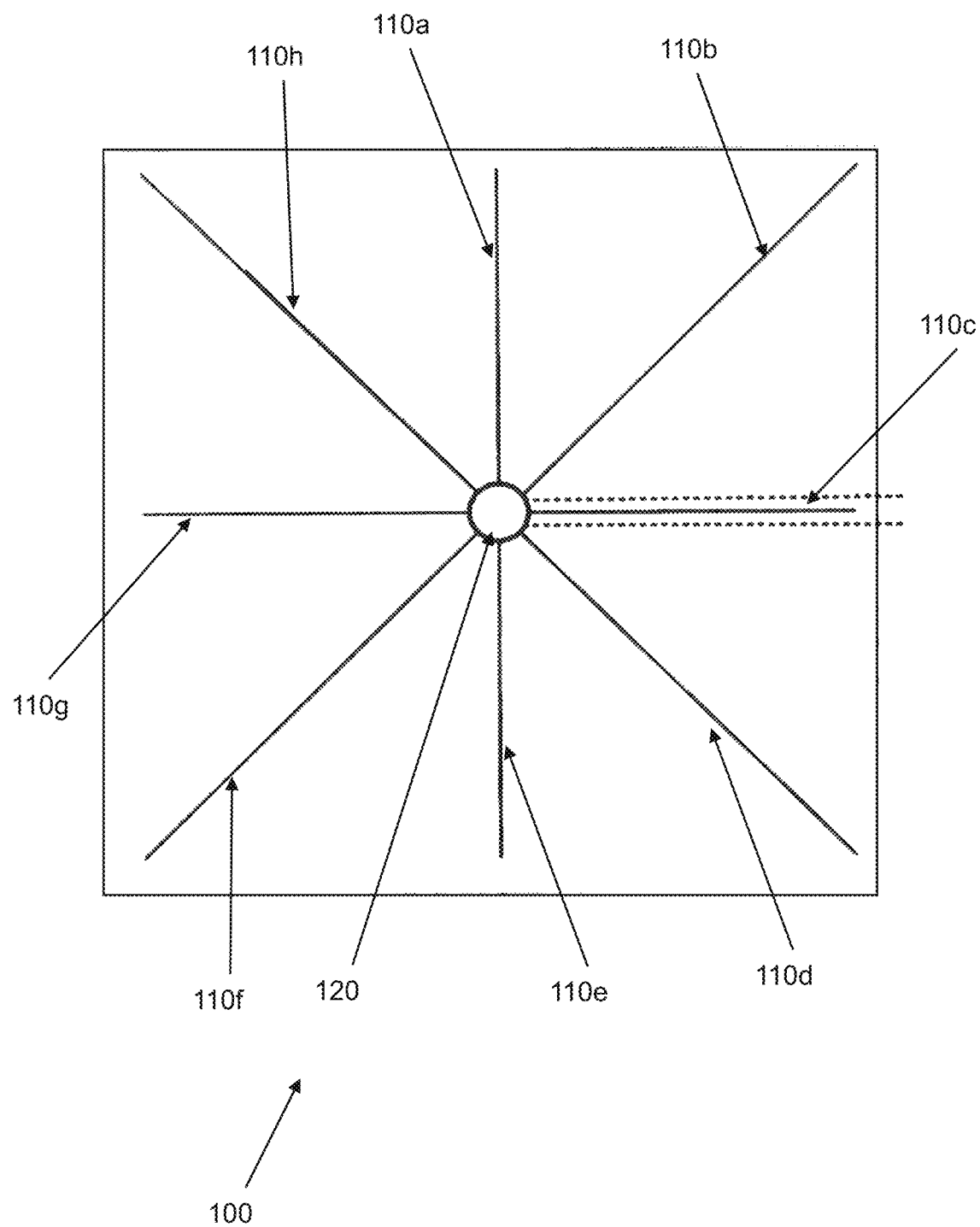
FIG. 1 is an overhead plan view of one embodiment of the radial exhaust of this invention.

FIG. 1 is an overhead plan view of one embodiment of the radial exhaust 100 of this invention. The radial exhaust 100 can include eight tubes 110*a*-110*h* positioned radially around a central hub 120. Each tube can include a sealed distal end and a plurality of lateral holes (not shown). Aerosol is delivered to the chamber bidirectionally using an opposed normal inlets from a common feed. A laminar flow element is placed under the inlet nozzles to create a mixing ante-chamber; and a radial exhaust manifold is implemented to improve flow symmetry. The radial exhaust contributes to less dead space leading to a T99 that more closely approximated the theoretical T99.

Figure 2:
FIG. 2 is a photograph of turbulent and rotational chamber flow.
Figure 3:
FIG. 3 is a photograph of turbulent and rotational chamber flow showing wall sampler location.
Figure 4:
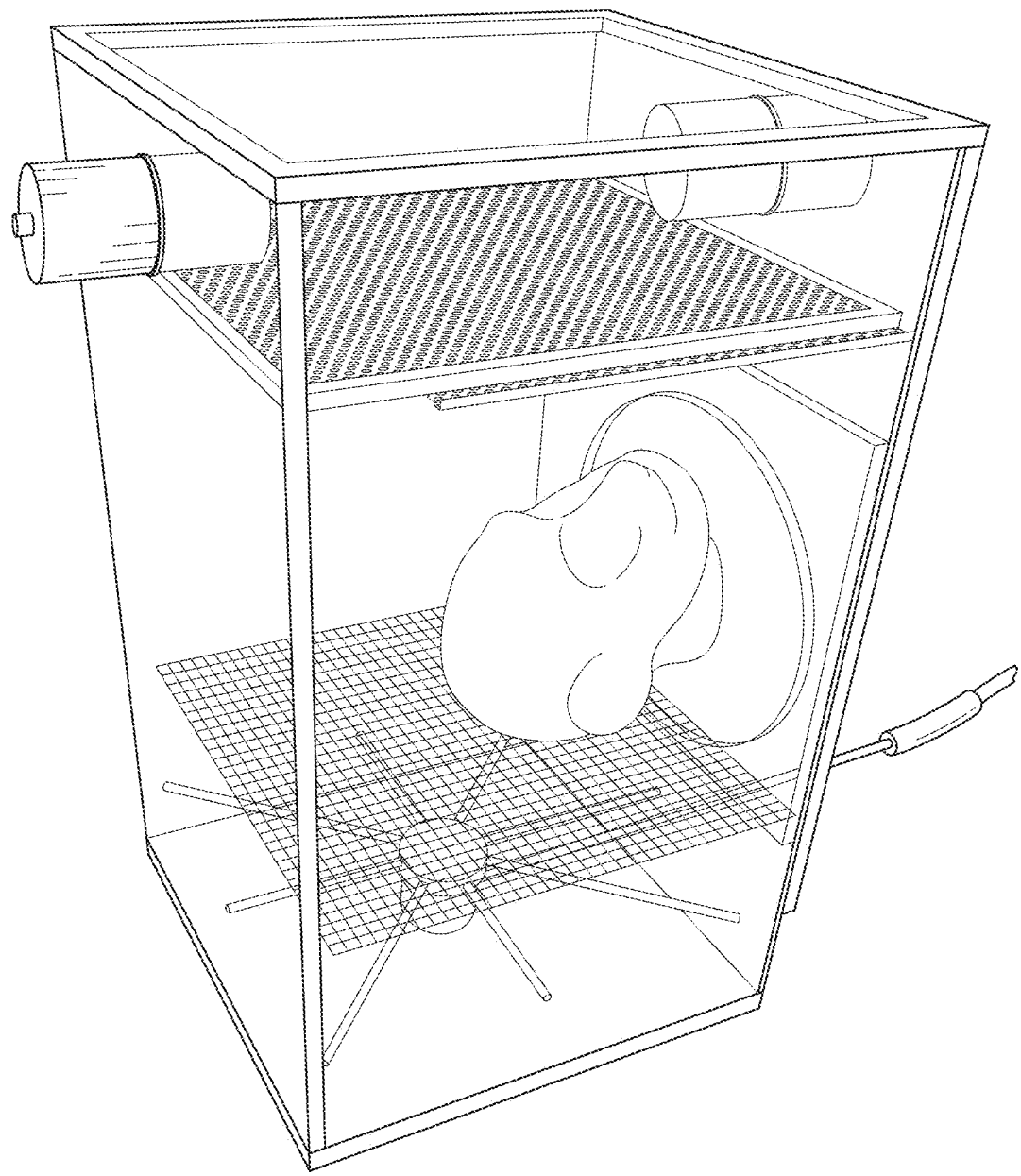
FIG. 4 illustrates one embodiment of the chamber assembly.

The head-only inhalation exposure chamber design currently in use at USAMRIID was evaluated using flow visualization techniques and industry standard aerosol tests to ascertain efficiency. The head-only chamber utilizes a 1.5 inch diameter by 12.0 inch long, unidirectional aerosol delivery line located at the top of the chamber, an aerosol sample collection port located at the midpoint of one wall of the chamber and a 1.5 inch diameter by 12.0 inch long opposed normal exhaust line. The aerosol delivery and exhaust lines are centrally located, continuous and have two 0.25 inch wide by 8.0 inch long slots positioned 180° apart. FIGS. 2 and 3 show the results of flow visualization tests that identified highly turbulent and rotational flow throughout the chamber that was directionally biased toward the location of the site where the nonhuman primate head rests (FIG. 2) and showed inefficient aerosol mixing at the aerosol sample collection location (FIG. 3). Tests using aerosol generated from a saline solution indicated that the measured time-to-99% stead-state aerosol concentration (T99) was less than the theoretical T99, which may be indicative of plug flow. Additionally, the percent dead space, a metric used to estimate chamber mixing efficiency (homogeneity) as measured from the wall sample collection port, was 47.7%. FIG. 4 also illustrates a perforated metal sheet between the laminar flow element and the radial exhaust, which can be used to support the test head. In at least one embodiment, the head-only chamber in the system is replaced with a whole body chamber.

Figure 5:
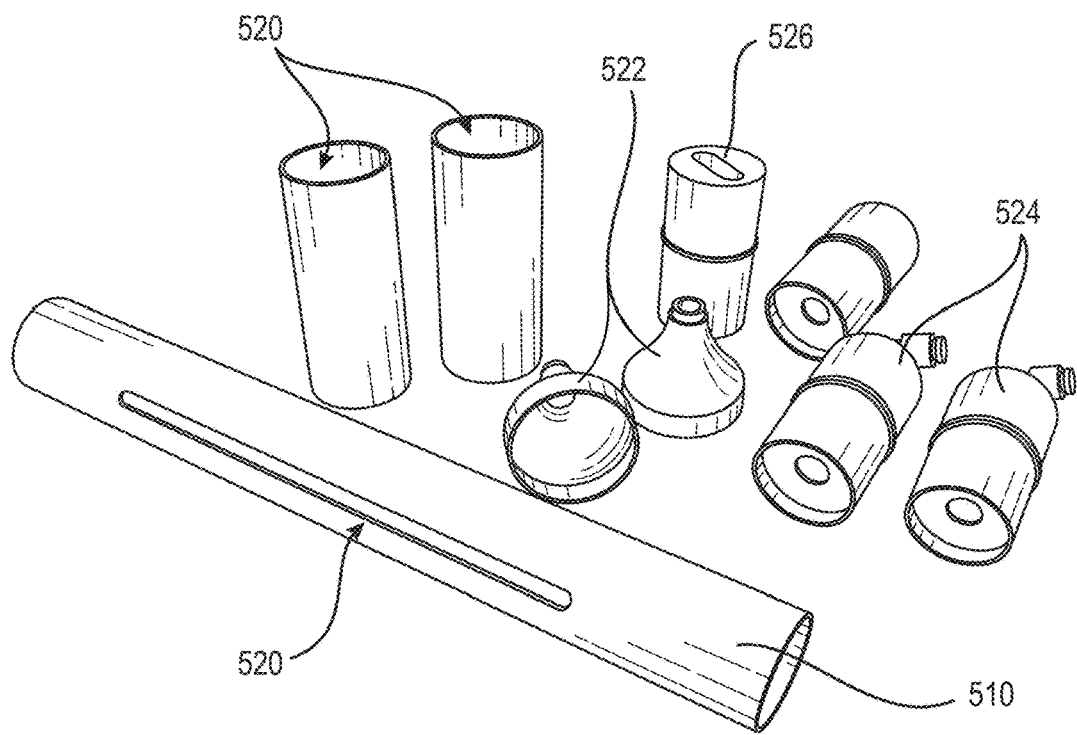
FIG. 5 illustrates different aerosol delivery line inlets.
Figure 6:
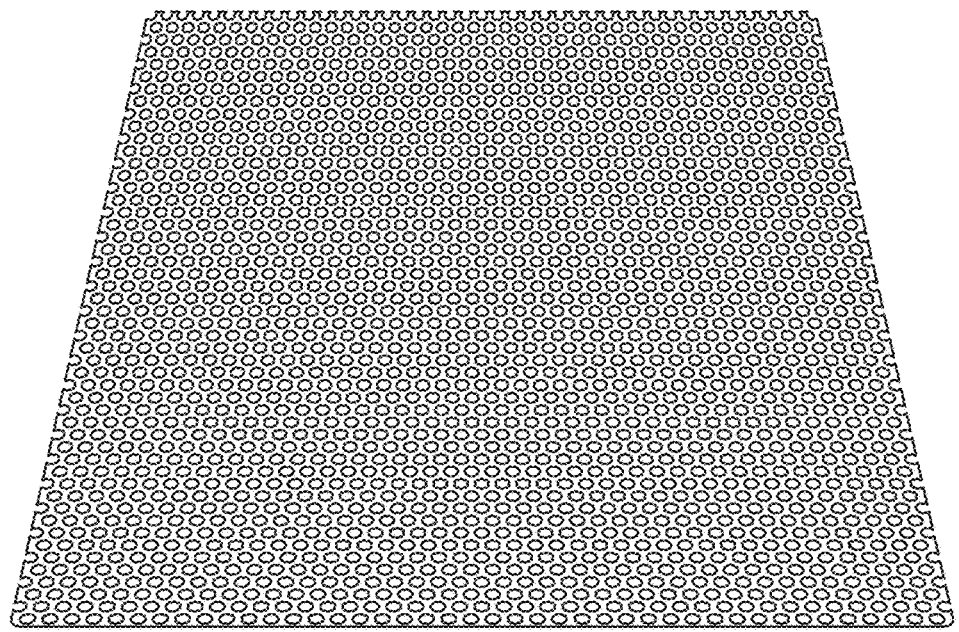
FIG. 6 illustrates one embodiment of the expanded metal laminar flow elements.
Figure 7:
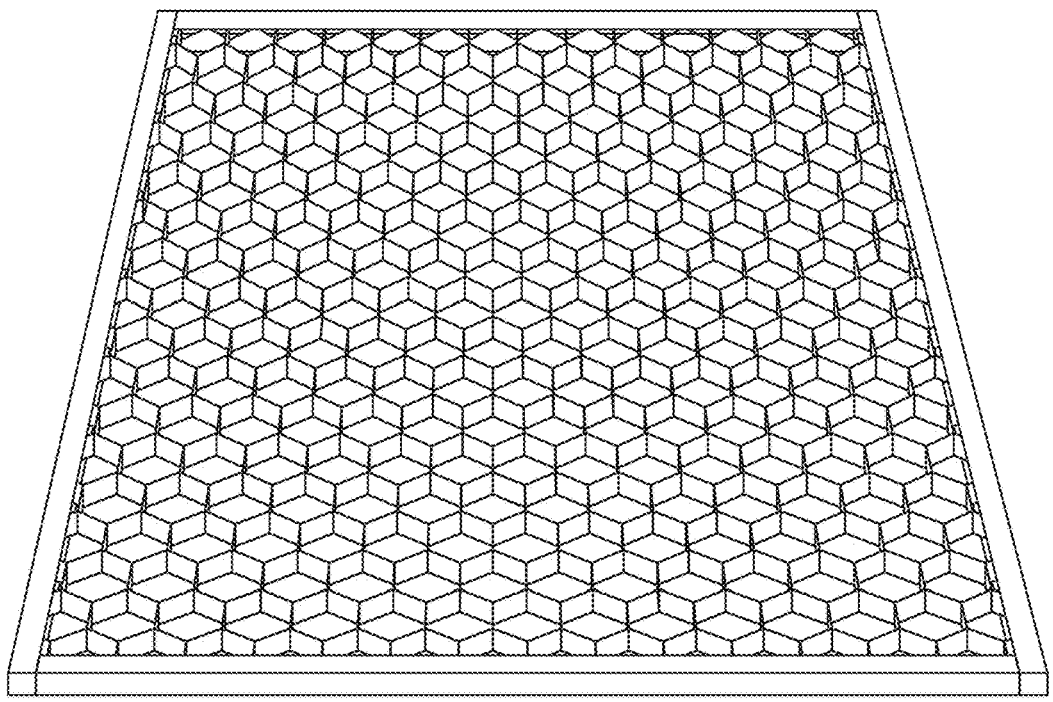
FIG. 7 illustrates one embodiment of the honeycomb laminar flow element.

Based on review and analysis of the flow visualization images and data collected from this head-only chamber, design modifications for the aerosol delivery line (inlet), a laminar flow element, the exhaust line were devised. A prototype chamber that included a simulated nonhuman primate head was assembled as shown in FIG. 4. The following modifications were tested:

An opposed normal, bidirectional aerosol delivery line strategy was implemented. One configuration used the existing 1.5 inch diameter continuous aerosol delivery line 510 that includes slots 512 on each side. The slots 512 were 0.25 inches in width by 8.0 inches in length and located perpendicularly to the vertical axis of the chamber. Other configurations included dual, non-continuous 1.5 inch diameter stainless steel tubing 520, dual non-continuous 0.5 inch diameter inlets 522, 524 and dual non-continuous 0.125 inch wide by 1.0 inch long slotted inlets 526. Aerosol Delivery Line Inlets tested are shown in FIG. 5.

Figure 8:
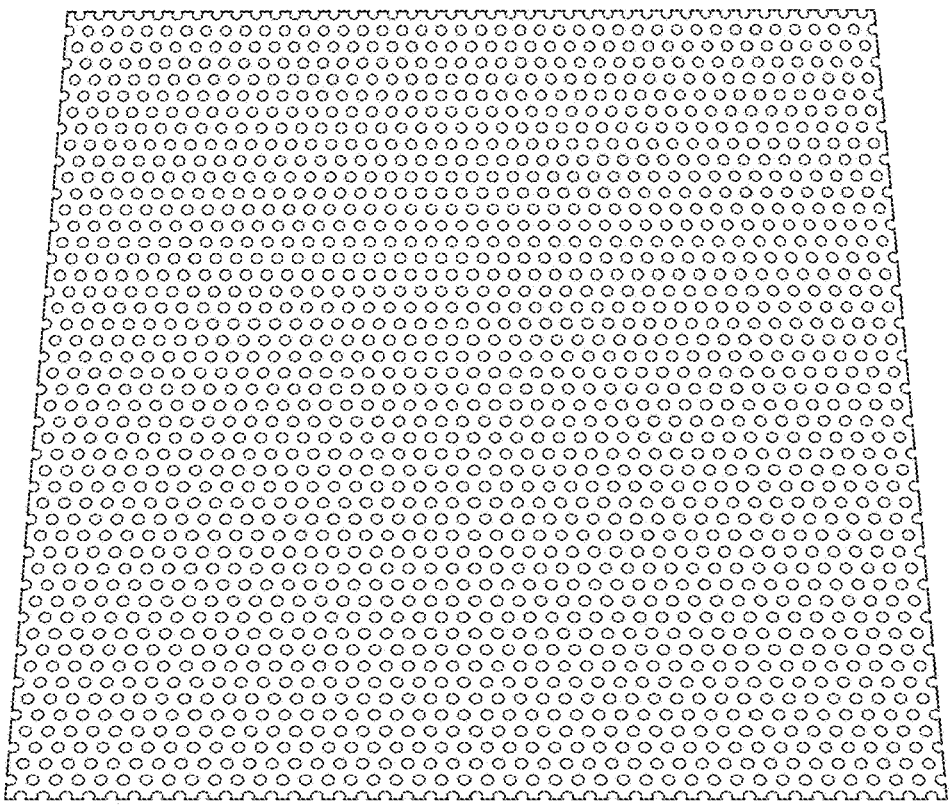
FIG. 8 illustrates one embodiment of the plastic laminar flow element.

Three types of laminar flow elements were tried below the aerosol delivery line forming an antechamber. Laminar flow elements tested included an 8.0×8.0×0.735 inch aluminum honeycomb (FIG. 6), an 8.0×8.0×0.0156 inch thick expanded metal sheet with 0.25 inch perforations (FIG. 7), and an 8.0×8.0×0.0625 inch thick plastic sheet with 0.0625 inch diameter perforations (FIG. 8).

The modified exhaust line consisted of eight 0.375 inch diameter stainless steel tubes positioned radially around a 1.5 inch diameter×2.0 inch (length) Plexiglas central hub. The distal end of each radial tube was sealed. Five 0.125 inch diameter jets were drilled along the length of each radial tube. In order to equilibrate the relative area each jet would exhaust, their locations along the length of the tube were calculated as:

$$r_m = l\sqrt{\frac{2m-1}{2n}}$$

$$0 < m \le n$$

Figure 9:
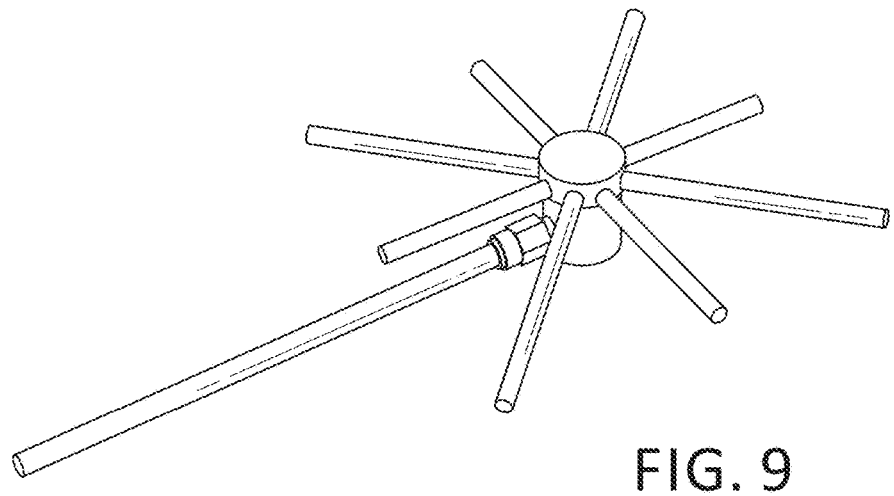
FIG. 9 illustrates one embodiment of the head-only chamber radial exhaust.

Where: r=radial location
m=number of jets to be located
n=total number of jets
l=length of the tube A single 0.375 inch diameter stainless steel tube was connected to the internal cavity of the central hub and supplied vacuum exhaust. For this study, the jets in each radial tube were aligned in a downward orientation. The modified radial exhaust is shown in FIG. 9.

Flow visualization tests identified highly turbulent flow throughout the chamber that were directionally biased toward the location of the site where the NHP head rests, but found inefficient aerosol mixing at the aerosol sample collection location. Tests using aerosol generated from a saline solution indicated that the measured time-to-99% stead-state aerosol concentration (T99) was less than the theoretical T99, which may be indicative of plug flow. Additionally, the percent dead space, a metric used to estimate chamber mixing efficiency (homogeneity), as measured from the wall sample collection port was 47.7%.

Each opposed normal delivery line configuration tested showed an improved distribution of the aerosol in the chamber as compared to the original, unidirectional design. The 1.5 inch diameter, slotted continuous inlet provided turbulent mixing in the antechamber, but produced a profound plug flow region in the center of the chamber and uneven mixing in the distal areas. The dual, non-continuous 1.5 inch diameter stainless steel tubing provided the least amount of turbulent mixing in the antechamber. The dual, non-continuous 0.5 inch diameter inlets and dual non-continuous 0.125 inch wide by 1.0 inch long slotted inlets provided the best turbulent mixing in the antechamber with the 0.5 inch diameter round jets providing the best mixing.

The aluminum honeycomb did not provide retention time of the aerosol in the antechamber and produced significant plug flow into the main chamber. The plastic sheet with 0.0625 inch perforations provided for adequate turbulent mixing in the antechamber and laminar flow in the main chamber, it restricted the flow of aerosol to the point that large globules of aerosol would plunge through the interior. The expanded metal sheet with 0.25 inch perforations performed the best of the laminar flow elements tested. It allowed for adequate retention time resulting in turbulent mixing in the antechamber and laminar flow in the main chamber. However, the 0.25 inch perforations restricted the flow in the center of the antechamber, resulting in the appearance of plug flow in the center of the main chamber. Nonetheless, the combination of a dual, non-continuous 0.5 inch diameter jet inlet with the expanded metal sheet with 0.25 inch perforations provided for the best overall mixing, laminar flow, stability and emptying observed during visual testing.

The radial exhaust resulted in improved laminar flow during chamber filling and chamber evacuation.

Figure 10:
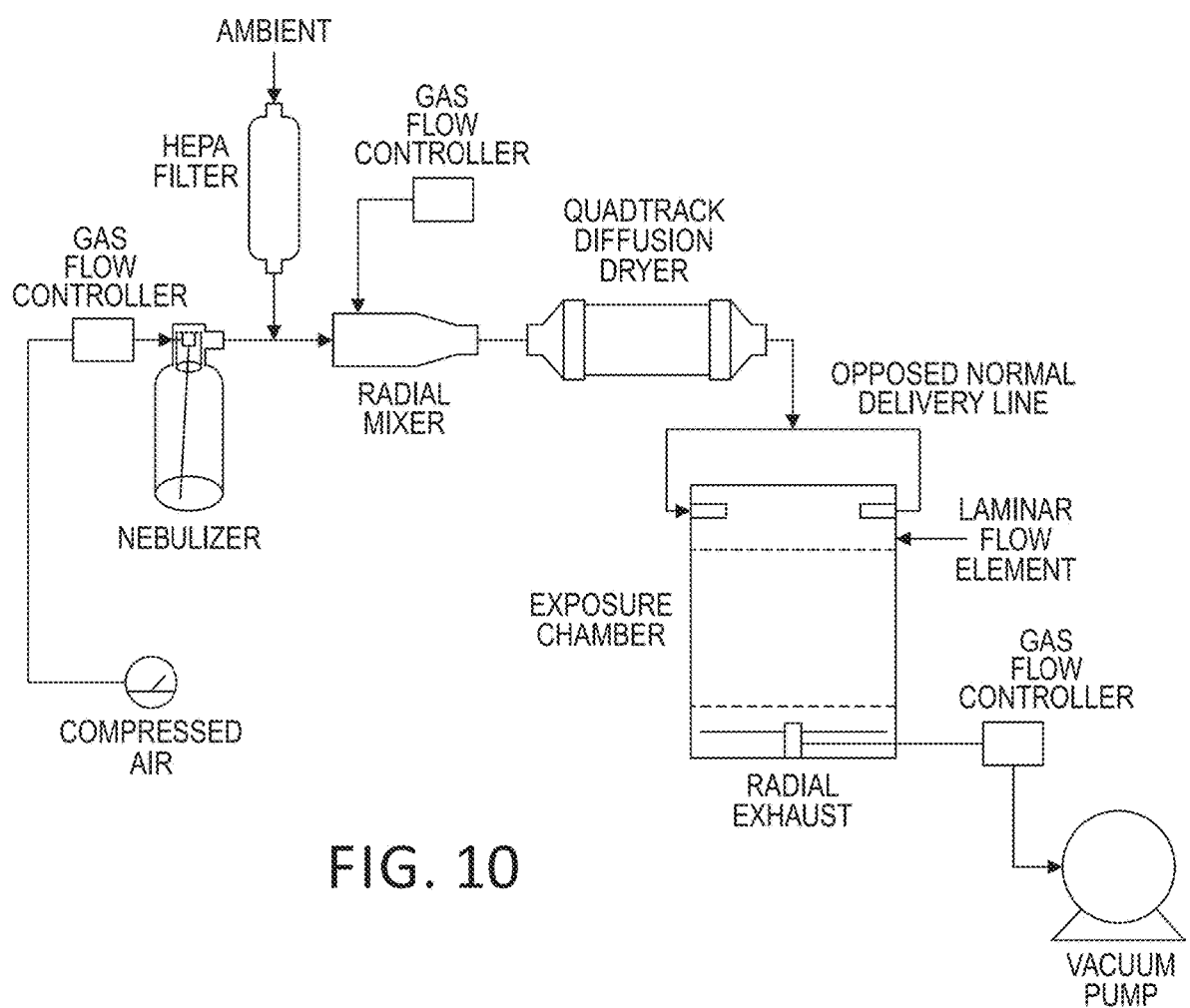
FIG. 10 is a schematic diagram of one embodiment of the modified chamber test system.

FIG. 10 is a schematic diagram of one embodiment of the modified chamber test system.

Compressed air can flow into a gas flow controller and a nebulizer. Ambient air can flow through a HEPA filter. The ambient air and compressed air from the nebulizer can flow into a radial mixer. The radial mixer can receive input from a gas flow controller. Air from the radial mixer can flow into a quadtrack diffusion dryer and into an opposed normal delivery line. The air can enter into the exposure chamber, out and through a gas flow controller, and into a vacuum pump.

Figure 11:
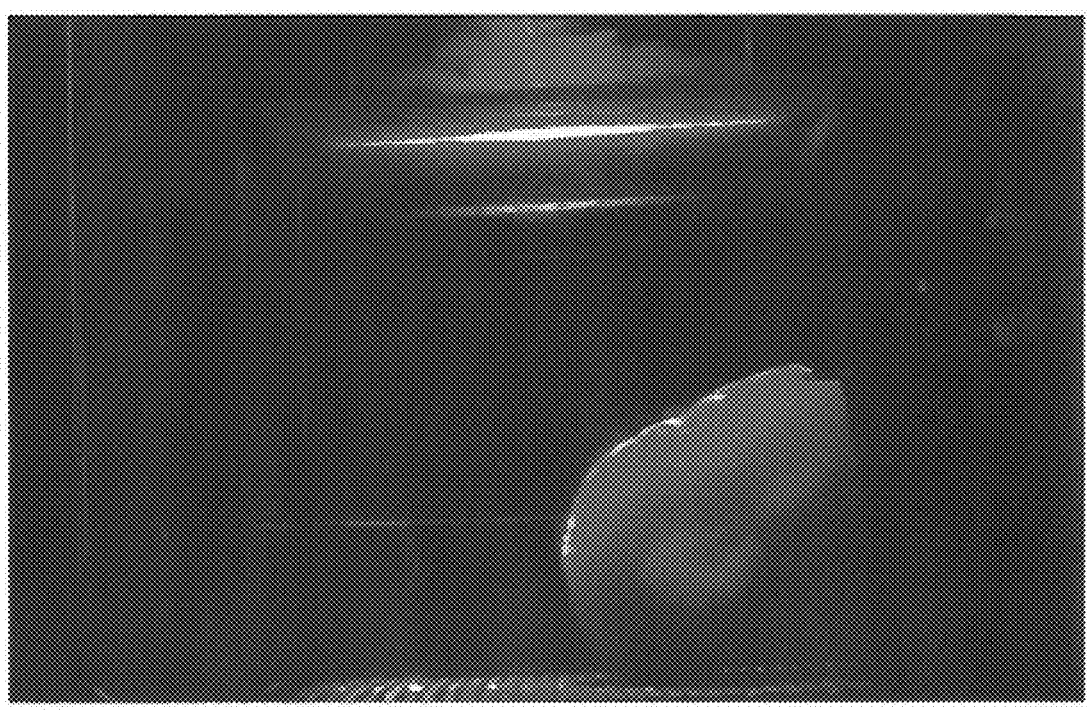
FIG. 11 is a photograph of the turbulent aerosol flow in antechamber.
Figure 12:
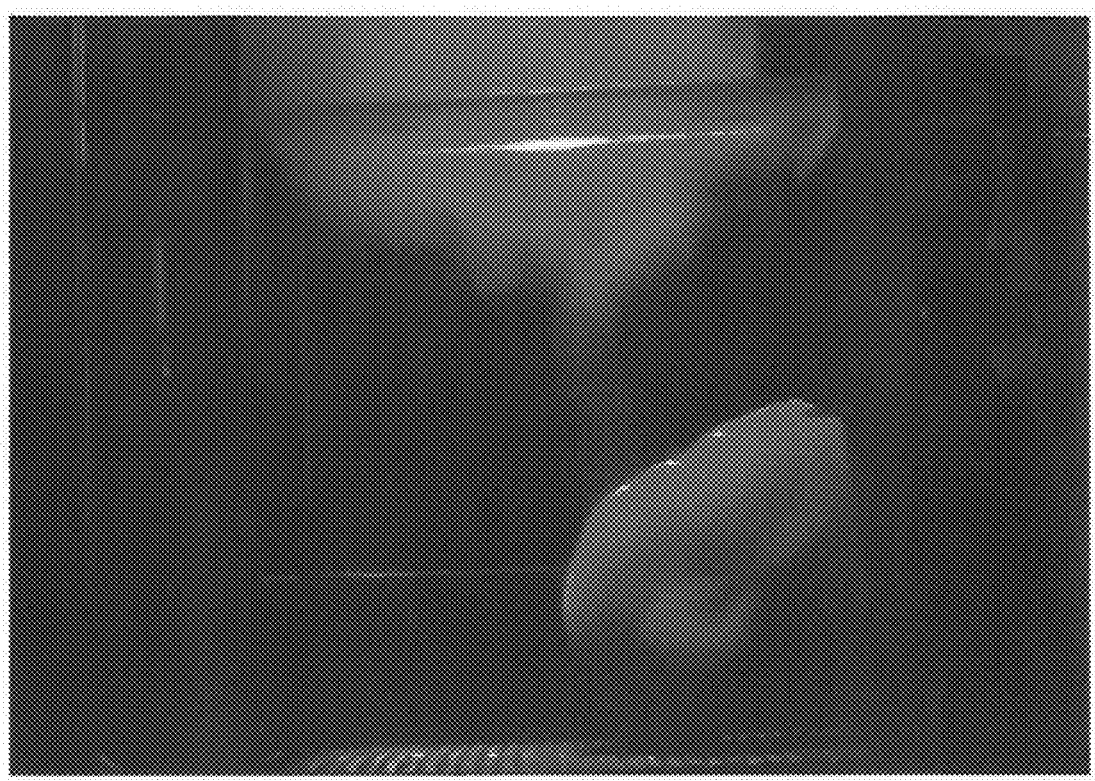
FIG. 12 is a photograph of a well-mixed chamber at steady state equilibrium.
Figure 17:
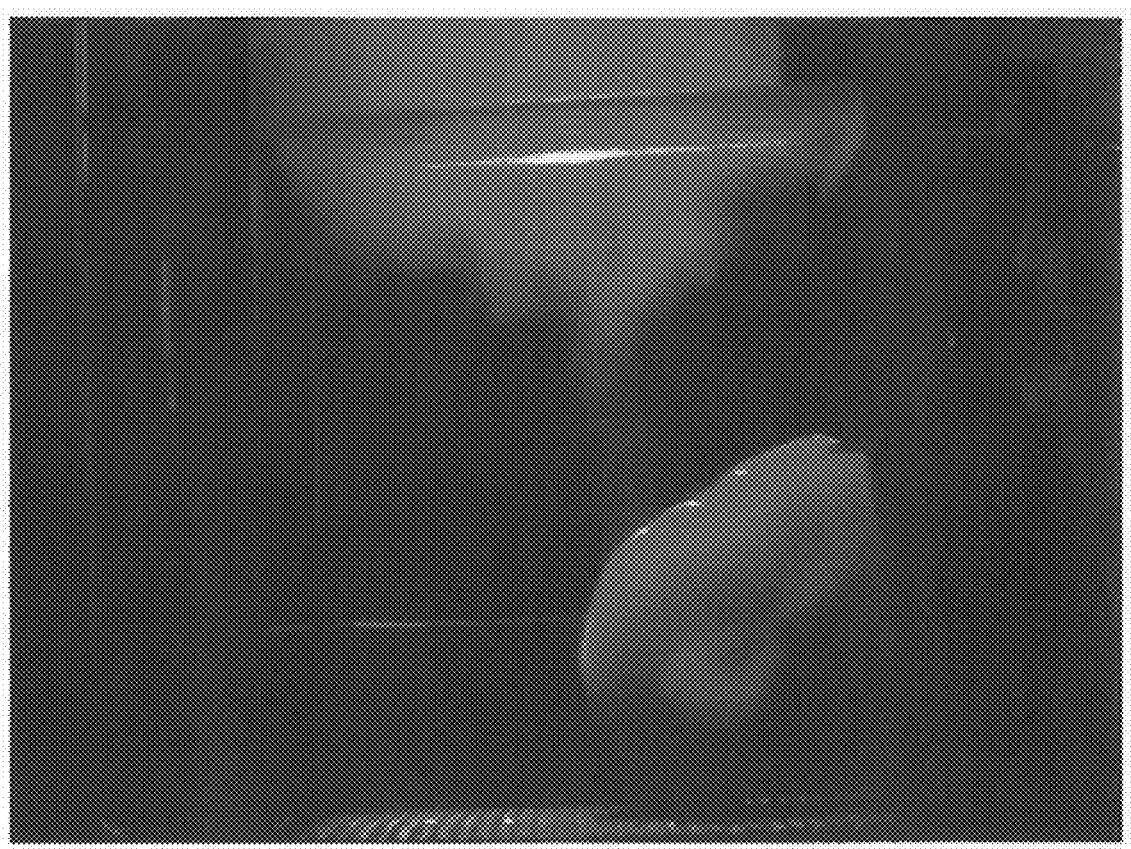
FIG. 17 is a photograph of laminar flow.

Flow visualization photographs of the modified head-only inhalation exposure chamber demonstrate a remarkable improvement in chamber flow dynamics. FIG. 11 shows turbulent mixing in the antechamber from the dual, non-continuous 0.5 inch diameter inlets. FIG. 17 demonstrates laminar flow of the aerosol as it penetrates the laminar flow element. FIG. 12 shows a well-mixed chamber at steady state equilibrium.

Figure 13:
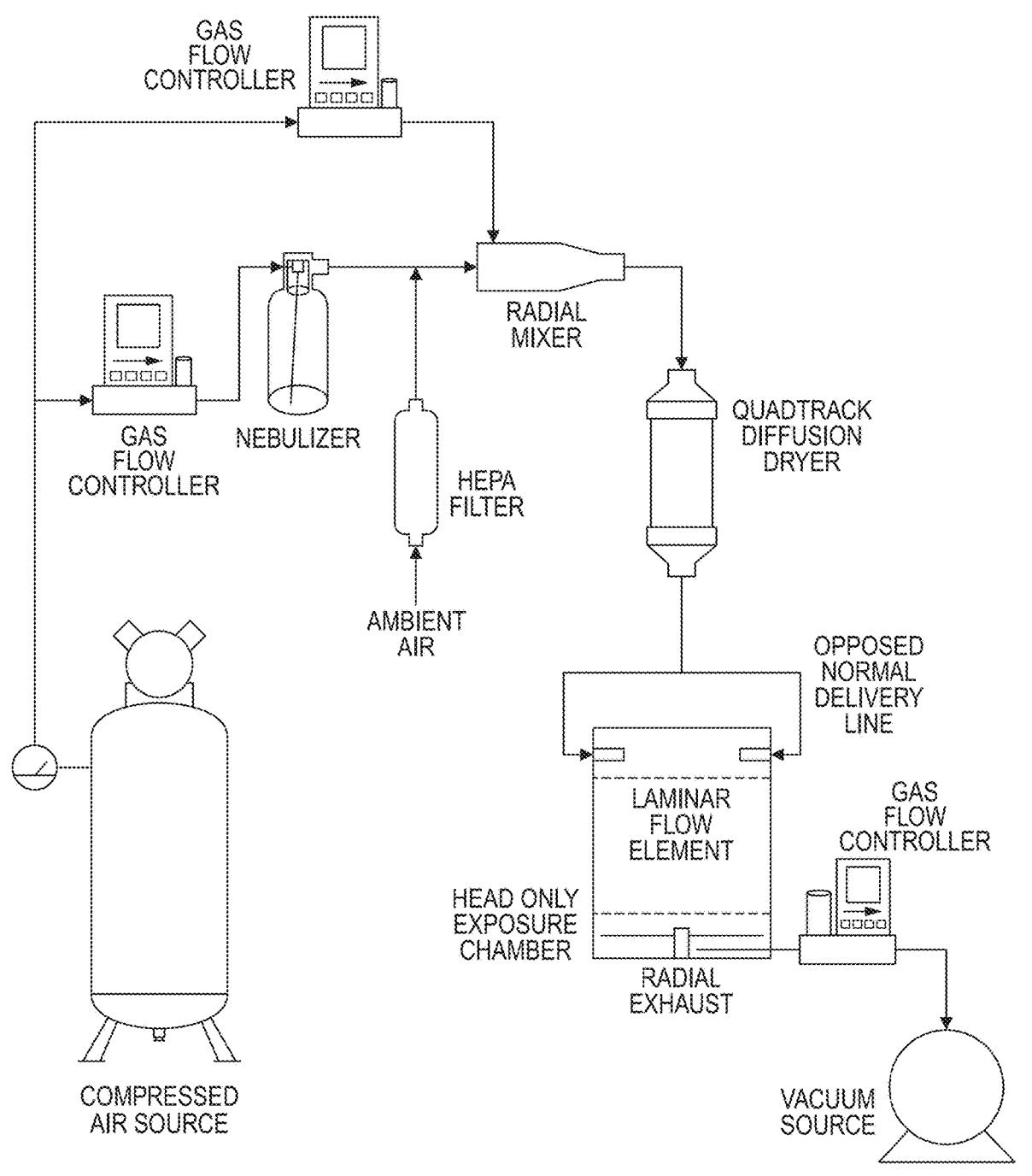
Figure 14:
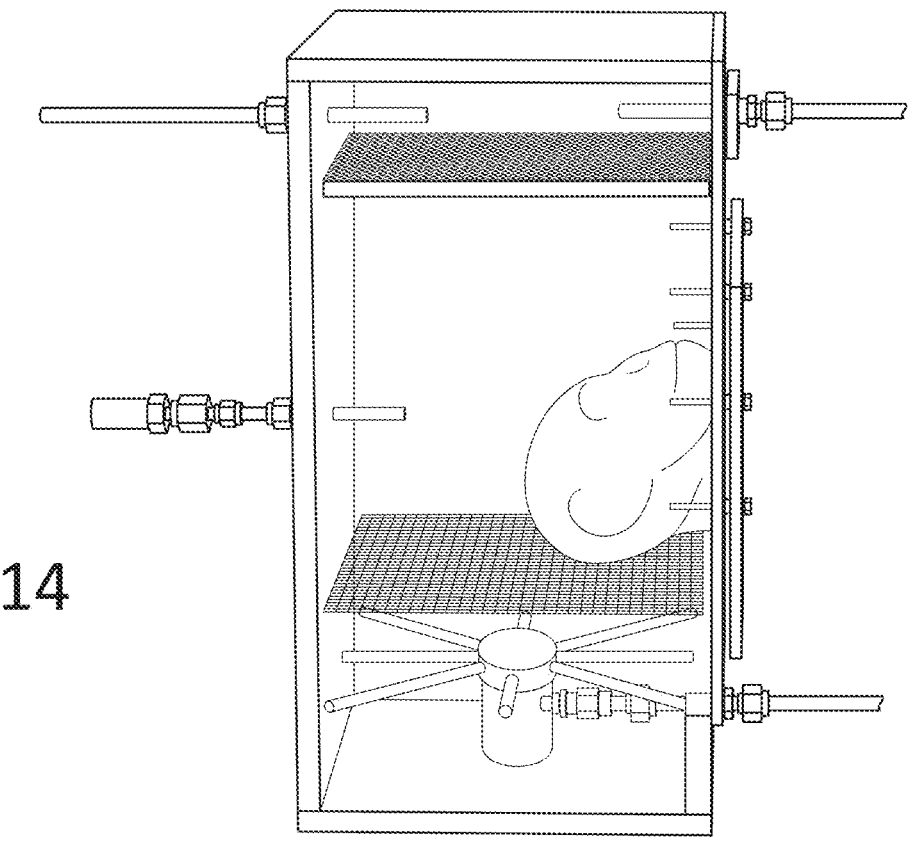
FIG. 14 illustrates a side-view of an embodiment of the novel head-only exposure chamber.

In one embodiment of the invention, a standard push-pull orientation was constructed using Alicat Gas Flow Controllers MCRS-100SLPM-TFT (vacuum exhaust), MC-30SLPM-D (radial mixer) and MC-30SLPM-TFT (nebulizer). A Model 11310, Lot D328105 Hope Nebulizer was filled with 30 mL of Silahydrocarbon MLO 86-348. Total exhaust volumetric flow through the chamber was set at 16.0 L/min. The volumetric flow rate of the radial mixer was set at 5.0 L/min and the volumetric flow rate through the nebulizer was set at 7.5 L/min. Aerosol was generated into the plenum until the concentration reached an approximate (visual) equilibrium and then stopped. The chamber aerosol concentration exponential rise, equilibrium and exponential decay were photographed and videotaped for subsequent analysis. A schematic of the modified chamber test system is shown in FIG. 13. One embodiment of the novel head-only exposure chamber is shown in FIG. 14.

Figure 15:
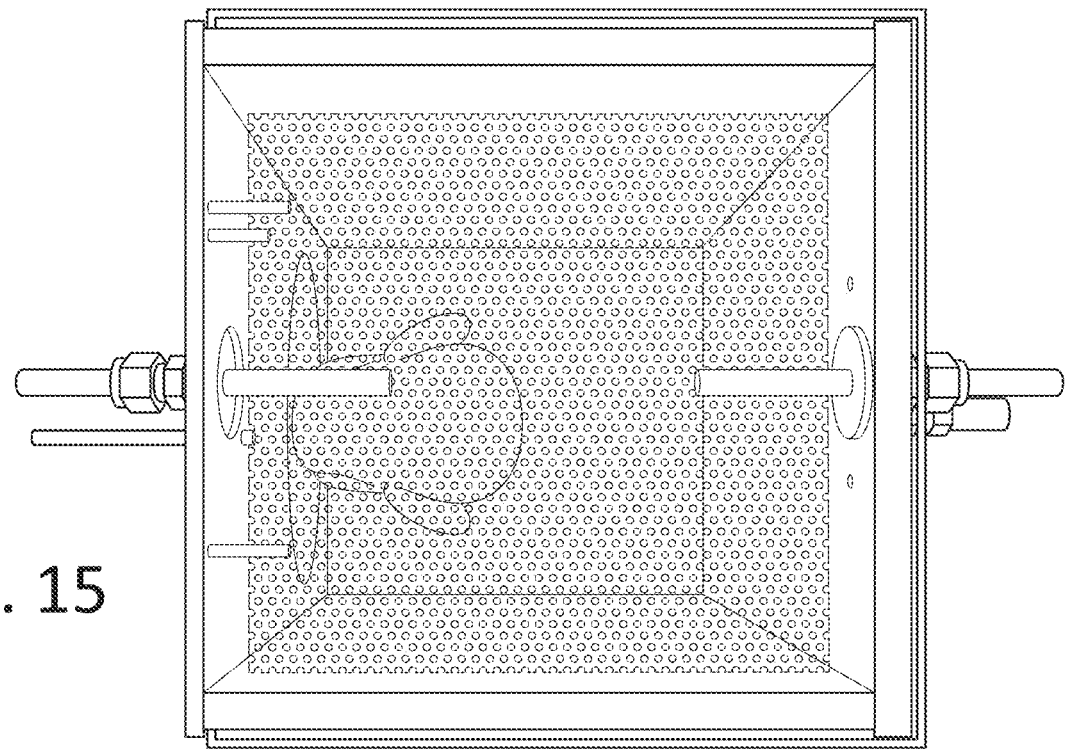
FIG. 15 illustrates a top-view of an embodiment of the novel opposed, normal, bidirectional aerosol delivery line.

In another embodiment of the invention, the opposed normal, bidirectional aerosol delivery line strategy was implemented. One configuration used the existing 1.5 inch diameter continuous aerosol delivery line 510 that includes slots 512 on each side. Aerosol was delivered to each end of the delivery line. Other configurations included dual, non-continuous 1.5 inch diameter stainless steel tubing 520, dual non-continuous 0.5 inch diameter inlets 522, 524 and dual non-continuous 0.125 inch wide by 1.0 inch long slotted inlets 526. The 0.375 inch noncontiguous opposed aerosol delivery lines is shown in FIG. 15.

In another embodiment of the invention, three types of laminar flow elements were tested. A 0.25 inch thick aluminum honeycomb did not provide retention time of the aerosol in the antechamber and produced significant plug flow into the main chamber. A 0.0625 inch plastic sheet with 0.0625 inch perforations provided for adequate turbulent mixing in the antechamber and laminar flow in the main chamber, however, it restricted the flow of aerosol to the point that large globules of aerosol would plunge through the interior. An expanded metal sheet with 0.25 inch perforations performed the best of the laminar flow elements tested. It allowed for adequate retention time resulting in turbulent mixing in the antechamber and laminar flow in the main chamber. However, the 0.25 inch perforations restricted the flow in the center of the antechamber resulting in the appearance of plug flow in the center of the main chamber. Nonetheless, the combination of a dual, non-continuous 0.375 in diameter aerosol inlet and the expanded metal sheet with 0.25 inch perforations provided for the best overall mixing, laminar flow, stability and emptying observed during visual testing.

The modified exhaust line consisted of eight 0.375 inch diameter stainless steel tubes positioned radially around a 1.5 inch diameter×2.0 inch (length) Plexiglas central hub. The distal end of each radial tube was sealed. Five 0.125 inch diameter jets were drilled along the length of each radial tube. In order to equilibrate the relative area each jet would exhaust, their locations along the length of the tube were calculated as:

$$r_m = l\sqrt{\frac{2m-1}{2n}}$$

$$0 < m \le n$$

Where: r=radial location
m=number of jets to be located
n=total number of jets
l=length of the tube A single 0.375 inch diameter stainless steel tube was connected to the internal cavity of the central hub and supplied vacuum exhaust. For this study, the jets in each radial tube were aligned in a downward orientation.

Figure 16:
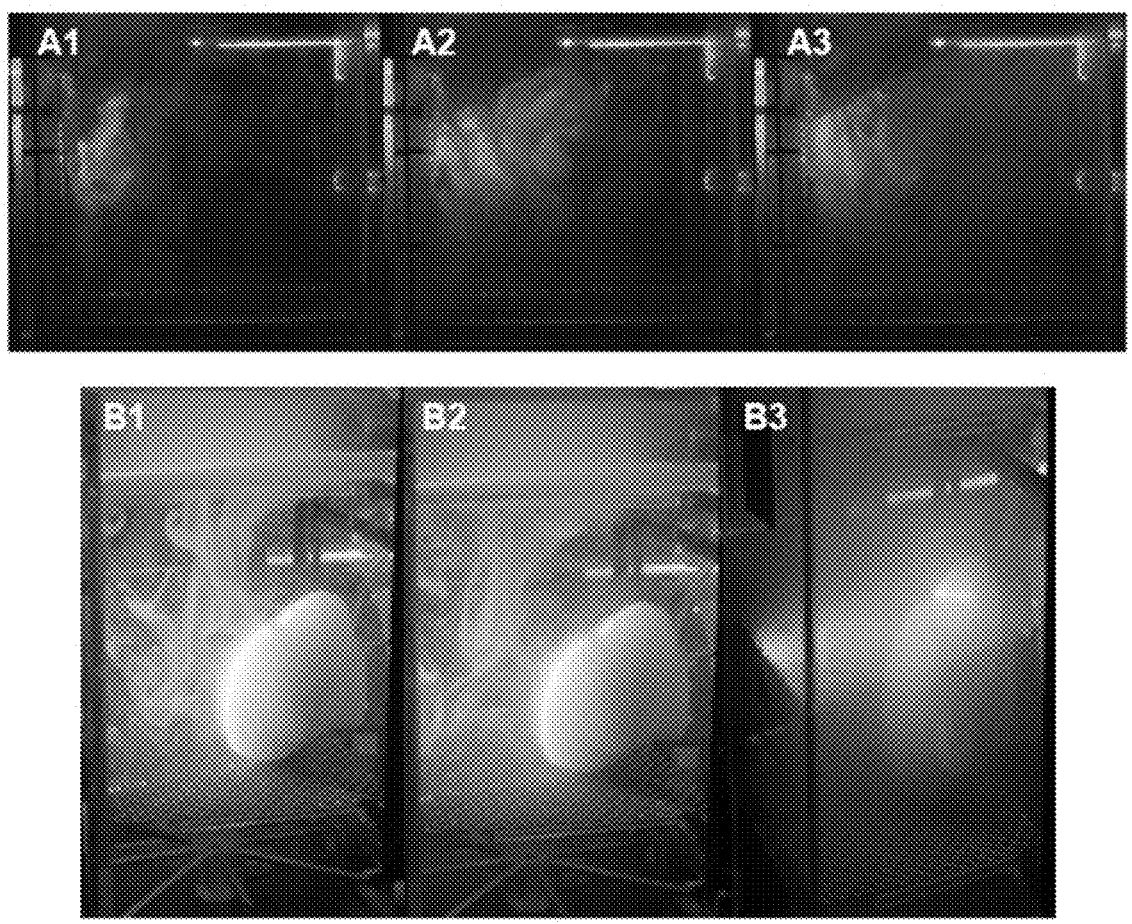
FIG. 16 illustrates time lapse comparison of low dynamics between the prior art exposure chamber and an embodiment of the present invention.

As seen in FIG. 16, a time lapse comparison of flow dynamics for (A) the original chamber design and (B) the modified chamber design. The original chamber design geometry produces large amounts of void space, even at steady state (Panel A3). The modified chamber design has a shorter time to steady state, and aerosol distribution is more uniform at steady state (Panel B3).

Chamber homogeneity (% Dead Space) in the current style head-only exposure chamber was determined using the equation:

$$\left(1 - \frac{T_{measured}}{T_{theoretical}}\right) \times 100\%$$

| Sample ID | V (L) | Q (L/min) | $T_{theoretical}$ (sec) | k (sec$^{-1}$) | $T_{measured}$ (sec) | Dead Space (%) |
|---|---|---|---|---|---|---|
| 1w | 16.256 | 16.000 | 60.9600 | 0.0304 | 32.8696 | 46.1 |
| 2w | 16.256 | 16.000 | 60.9600 | 0.0285 | 35.1246 | 42.4 |
| 3w | 16.256 | 16.000 | 60.9600 | 0.0363 | 27.5614 | 54.8 |
| MEAN | | | | 0.0317 | 31.8519 | 47.7 |
| STDEV | | | | 0.0041 | 3.8829 | 6.4 |
| % CV | | | | 12.8 | 12.2 | 13.3 |
| 1c | 16.256 | 16.000 | 60.9600 | 0.0382 | 26.1536 | 57.1 |
| 2c | 16.256 | 16.000 | 60.9600 | 0.0500 | 20.0182 | 67.2 |
| 3c | 16.256 | 16.000 | 60.9600 | 0.0402 | 24.8825 | 59.2 |
| 4c | 16.256 | 16.000 | 60.9600 | 0.0441 | 22.6783 | 62.8 |
| MEAN | | | | 0.0431 | 23.4331 | 61.6 |
| STDEV | | | | 0.0052 | 2.6915 | 4.4 |
| % CV | | | | 12.0 | 11.5 | 7.2 |

Triplicate aerosol samples were collected from either a wall sampling location (w) or from a sample probe positioned at the approximate location of the animal's nose (c).

| ID | V (L) | Q (L/min) | $T_{theoretical}$ (sec) | k (sec$^{-1}$) | $T_{measured}$ (sec) | Dead Space (%) |
|---|---|---|---|---|---|---|
| 1 | 16.256 | 16.000 | 60.9600 | 0.0209 | 47.8469 | 21.5 |
| 2 | 16.256 | 16.000 | 60.9600 | 0.0230 | 43.4783 | 28.7 |
| 3 | 16.256 | 16.000 | 60.9600 | 0.0251 | 39.8406 | 34.6 |
| MEAN | | | | 0.0230 | 43.7219 | 28.3 |
| STDEV | | | | 0.0021 | 4.0087 | 6.6 |
| % CV | | | | 9.1 | 9.2 | 23.3 |

Triplicate aerosol samples were collected from a sample probe positioned at the approximate location of the animal's nose (c).

| | Current Chamber Design $T_{99}$ (min) | Modified Chamber Design $T_{99}$ (min) |
|---|---|---|
| | 2.9 | 3.7 |
| | 2.8 | 3.3 |
| | 2.7 | 3.1 |
| MEAN | 2.8 | 3.4 |
| STDEV | 0.1 | 0.3 |

The observed time-to-99% (T99) steady state aerosol concentration was determined in the current and modified head-only exposure chambers using 2 μm (nominal) polystyrene latex microspheres. Triplicate samples were collected from each chamber style. The mean T99 for the current head-only style exposure chamber was 2.8±0.1 min. The mean T99 for the modified head-only style exposure chamber was 3.4±0.3 min. The theoretical T99 for each style of chamber, as calculated using the equation given by Cheng and Moss (1), was 4.63 min.

Redesigning the aerosol exposure chamber with a turbulent mixing antechamber and a radial exhaust to facilitate fluid dynamic symmetry in the direction of flow within the chamber resulted in a more efficient design. Incorporating the new design elements led to a decrease in dead space and a measured T99 that more closely approximated the theoretical T99. Testing with a visible aerosol confirmed a turbulent mixing zone in the antechamber and laminar aerosol flow throughout the rest of the chamber.

Additional optional embodiments to the above-described embodiments include, but are not limited to: modifications of the dual, non-continuous opposed normal aerosol delivery line to maximize turbulent mixing; modifications may include slightly offsetting the jets and adjusting the length of the tubes; modifications of the laminar flow element will include adjusting the diameter of the perforations in the expanded metal sheet and overlaying multiple sheets to restrict flow enough to allow for optimal mixing while providing laminar flow with minimized globule formation; and, any combination of these modifications. Tests with the radial exhaust will include different orientations of the jets in the radial tubes. In at least one embodiment, additional tests include the addition of a 0.25 inch diameter stainless steel sample probe and ventilation and temperature regulation of the simulated nonhuman primate head to determine the effects on chamber laminar flow and mixing.

Figure 18:
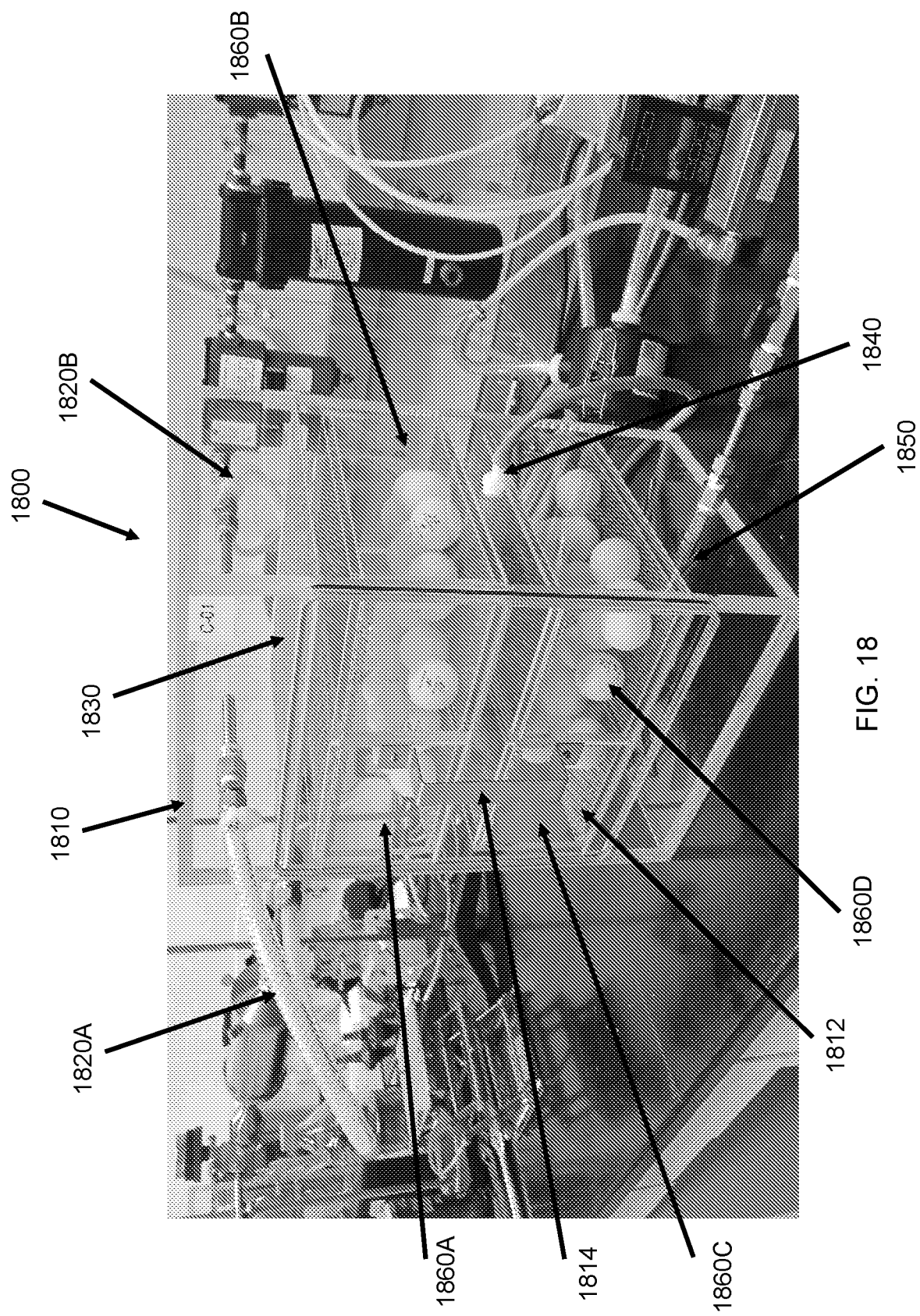
FIG. 18 illustrates an inhalation exposure chamber system according to an embodiment of the invention.

FIG. 18 illustrates a whole body exposure system 1800 according to an embodiment of the invention, where the system 1800 includes an inhalation exposure chamber 1810, aerosol delivery lines 1820A and 1820B, a laminar flow element 1830, an aerosol sample collection port 1840 (also referred to herein as a sampling tube), a radial exhaust 1850, cage 1860A, cage 1860B, cage 1860C, and cage 1860D. Each cage can include an upper wall, a bottom wall, and four side walls. The sidewalls can be formed from a transparent material (e.g., plastic, glass). The upper wall and the bottom wall can be formed from a transparent material or a perforated sheet. The inhalation exposure chamber 1810 can include a door 1812 and handle 1814.

FIG. 19A is a top perspective view of an alternative inhalation exposure chamber system 1900 according to another embodiment of the invention. FIG. 19B is a top view of the inhalation exposure chamber system illustrated in FIG. 19A. FIG. 19C is a side view of the inhalation exposure chamber system illustrated in FIG. 19A. FIG. 19D is a side cross-sectional view of the inhalation exposure chamber system illustrated in FIG. 19A. The whole body inhalation exposure chamber system 1900 can include an inhalation exposure chamber 1910, aerosol delivery ports 1920A and 1920B, laminar flow element 1930A, 1930B and 1930C, aerosol sample collection ports 1940A and 1940B, and a radial exhaust 1950.

As illustrated in FIG. 23, at least one embodiment of the invention provides an Automated Bioaerosol Exposure System (ABES) 2310. The system 2310 includes a control unit 2320 having software 2322 and being interconnected with an Aerodynamic Particle Sizer (APS) 2334. The system 2310 includes an exposure chamber 2330 such as a head-only exposure chamber 2332 or a whole body exposure chamber 2334.

As illustrated in FIG. 24, at least one embodiment of the invention provides an Integrated Modular Bioaerosol Respiratory Exposure System (IMBRE) 2410 that includes a pneumatic/electronic control box 2420 and accompanying control computer program instructions 2422 that can utilize existing aerosol exposure chambers 2440 (e.g., COTS nose-only exposure chambers 2444, whole body exposure chambers 2446, or an oronasal mask 2448) with a plethysmography interface 2442. The IMBRE system 2410 (also referred to herein as the "system") can interface with particle sizing and counting devices 2424 that provide data streams to the computer program instructions 2422, which can enable the control of exposure duration based on aerosol particle count (which can be correlated with presented dose). The system 2410 may also include environmental controls 2430 with humidity control 2432 and aerosol ageing 2434.

Additionally, the system can count aerosol particles and correlate particle counts with presented dose and determine particle size distribution. This feature can be used to determine the time required for "dose-calculated" exposures. More specifically, aerosol particles can be diluted and collected from one sample tube using an in-line aerosol particle counter. Aerosol particles can be collected from a second sample tube using filters and liquid impingers. Samples from each mask can be collected over different lengths of time. The filter samples can be weighed and a mass per unit volume aerosol concentration calculated. The liquid impinger samples can be microbiologically assayed and a count per unit volume aerosol concentration can be calculated. The mass and count per unit volume aerosol concentrations can be plotted against the count data from the in-line particle counter and a mathematical regression correlation can be determined. The mathematical correlation can be used to determine dosimetry of subsequent exposures.

At least one embodiment of the invention provides a compact and modular system that runs aerosol exposures using a head-only exposure chamber or a whole body exposure chamber. The system can expose animal experimental models to biological, chemical, and radiological agents for pathogenesis and/or toxicity studies for therapeutic, vaccine, and/or prophylactic development. The system can also be used to test aerosolized drug formulations in animal models to facilitate the development of inhalable drugs within the pharmaceutical industry.

In at least one embodiment, the system provides improved spray accuracy, including integrated real-time plethysmography, particle-based tracking of concentration (oronasal mask module), real-time adjustment of exposure time, and/or continuous spray improvement based on previous run data across all systems (animal, agent, agent media, etc.). The system 2410 may also provide spray analysis and reporting, integrated calibration 2428 of all components, and/or system health detection and analysis. Specifically, the system may detect the likelihood of component failure before any run and ensure that all components and/or accessories are in calibration before each spray, where component heath and calibration can be transferable to other systems.

FIG. 20 is a flow diagram illustrating a method for controlling aerosol respiratory exposure according to an embodiment of the invention, where the exposure chamber includes a differential pressure transmitter. The differential pressure transmitter can detect positive pressure pulses and negative pressure pulses in the exposure chamber 2010. Specifically, a differential pressure transducer can generate a pressure differential waveform and transmit the pressure differential waveform to a processor for further calculation.

Plethysmography software 2426 in the processor can determine tidal volume and frequency based on the detected positive and negative pressure pulses 2020. The processor can also calculate the respiratory minute volume 2030, which may be a product of the tidal volume and the frequency. In at least one embodiment, the respiratory minute volume is an average integral over a respiratory waveform, where the respiratory waveform is measured, integrated over time, and averaged.

The processor can calculate the cumulative inspired volume 2040, which may be a product of the respiratory minute volume and an exposure duration. The cumulative inspired volume can be calculated by integrating the respiratory waveform over time in real-time until the desired presented dose is achieved. The processor can also calculate the desired inhaled volume of aerosol with the cumulative inspired volume and the theoretical aerosol concentration 2050. The total presented dose can be an integral of the product of a concentration function and a volume function over time when aerosol concentration changes over time.

FIG. 21 is a flow diagram illustrating a method for controlling aerosol respiratory exposure according to an embodiment of the invention. The method can also determine aerosol particle size distribution (mass median aerodynamic diameter (μm)) and geometric standard deviation or particle counts. An in-line aerosol particle counter can collect first aerosol particles from a first aerosol sample collection port for a first time duration 2110. A second aerosol sample collection port can collect second aerosol particles using one or more filters and one or more liquid impingers 2120. The second aerosol particles can be collected for a second time duration that is different from the first time duration.

In at least one embodiment, the weights of the filters in the second aerosol sample collection port is determined 2130; and, a mass per unit volume aerosol concentration is calculated based on the weights of the filters 2140. Second aerosol particles from the liquid impinger can be microbiologically assayed 2150; and, a count per unit volume aerosol concentration can be calculated based on the microbiological assay 2160.

The mass per unit volume aerosol concentration and the count per unit volume aerosol concentration can be plotted against count data from the in-line aerosol particle counter to correlate a presented dose with the particle count 2170. A mathematical regression correlation can be determined based on the plotting of the mass per unit volume aerosol concentration and the count per unit volume aerosol concentration against the count data from the in-line aerosol particle counter 2180. Dosimetry of subsequent exposures can be determined based on the mathematical regression correlation 2190.

Referring now to FIG. 22, a representative a hardware environment for practicing at least the first embodiment of the invention is depicted. This schematic drawing illustrates a hardware configuration of an information handling/computer system in accordance with at least one embodiment of the invention. The system comprises at least one processor or central processing unit (CPU) 2210. The CPUs 2210 are interconnected with system bus 2212 to various devices such as a random access memory (RAM) 2214, read-only memory (ROM) 2216, and an input/output (I/O) adapter 2218. The I/O adapter 2218 can connect to peripheral devices, such as disk units 2211 and tape drives 2213, or other program storage devices that are readable by the system. The system can read the inventive instructions on the program storage devices and follow these instructions to execute the methodology of at least one embodiment of the invention. The system further includes a user interface adapter 2219 that connects a keyboard 2215, mouse 2217, speaker 2224, microphone 2222, and/or other user interface devices such as a touch screen device (not shown) to the bus 2222 to gather user input. Additionally, a communication adapter 2220 connects the bus 2222 to a data processing network 2225, and a display adapter 2221 connects the bus 2222 to a display device 2223 which may be embodied as an output device such as a monitor, printer, or transmitter, for example.

The flowchart and block diagrams in the FIGS. figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the FIGS. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

Although the present invention has been described in terms of particular example embodiments, it is not limited to those embodiments. The embodiments, examples, and modifications which would still be encompassed by the invention may be made by those skilled in the art, particularly in light of the foregoing teachings.

As used above "in fluid communication" is intended to indicate that two components are in fluid communication with each other and that fluid is able to pass from one component to another component directly or indirectly.

As used above "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and, preferably, approaching or approximating such a physical or functional characteristic.

Those skilled in the art will appreciate that various adaptations and modifications of the exemplary and alternative embodiments described above can be configured without departing from the scope and spirit of the invention. Therefore, it is to be understood that, within the scope of the appended claims, the invention may be practiced other than as specifically described herein.

While particular embodiments of the present invention have been shown and described, it will be obvious to those skilled in the art that changes and modifications may be made without departing from this invention. Therefore, it is intended that the claims herein are to include all such obvious changes and modifications as fall within the true spirit and scope of this invention.

VI. INDUSTRIAL APPLICABILITY

A system featuring a head-only or whole body inhalation exposure chamber and a method of opposed, normal, bidirectional aerosol delivery. The system includes a laminar flow element and a radial exhaust.

VII. REFERENCE

The teachings of the references cited herein are incorporated herein in their entirety: McClellan, R. O and Henderson, R. E. (edited). Concepts in Inhalation Toxicology. Hemisphere Publishing Corporation, p 45-48. 1989.

What is claimed:

1. A system comprising:

an inhalation exposure chamber having an ante-chamber;

an aerosol delivery line connected to said inhalation exposure chamber, said aerosol delivery line configured to produce a bi-directional and symmetrical presentation of aerosol to the ante-chamber of said inhalation exposure chamber;

a laminar flow element defining the ante-chamber where-mixing of the aerosol occurs; and a radial exhaust having a plurality of radial exhaust tubes extending radially out from a central hub, and wherein said radial exhaust and said laminar flow element enable laminar flow of the aerosol through said inhalation exposure chamber.

2. The system according to claim 1, wherein said aerosol delivery line is centrally located at a top of said inhalation exposure chamber, wherein said laminar flow element is located below said aerosol delivery line, and wherein said radial exhaust is centrally located at a bottom of said inhalation exposure chamber.

3. The system according to claim 1, further comprising at least one sample collection port located at a midpoint of a wall of said inhalation exposure chamber and below said laminar flow element.

4. The system according to claim 1, further including at least one additional laminar flow element, said at least one additional laminar flow element includes a sheet having a plurality of perforations.

5. The system according to claim 1, wherein said radial exhaust tubes includes eight tubes positioned radially around said central hub, wherein each tube includes a sealed distal end and a plurality of lateral holes.

6. The system according to claim 5, wherein said eight radial exhaust tubes includes four first tubes having a first length and four second tubes having a second length, wherein said second length is greater than said first length.

7. The system according to claim 1, wherein said aerosol delivery line includes a 12.0 inch long pipe having a 1.5 inch diameter, said pipe passes through said ante-chamber.

8. The system according to claim 1, wherein said aerosol delivery line includes a pipe passing through said inhalation chamber and said pipe having two 0.25 inch wide by 8.0 inch long slots positioned 180° apart.

9. The system according to claim 1, wherein said laminar flow element includes an 8.0 inch×8.0 inch×0.0625 inch sheet with 0.0625 inch diameter perforations.

10. The system according to claim 1, wherein said radial exhaust tubes include 0.375 inch diameter tubes positioned radially around said central hub, said central hub having a 1.5 inch diameter and a 2.0 inch height.

11. The system according to claim 10, wherein each of said radial exhaust tubes includes a sealed distal end and five 0.125 inch diameter lateral apertures.

12. The system according to claim 1, further comprising at least two cages in said inhalation exposure chamber.

13. The system according to claim 1, wherein said inhalation exposure chamber includes four sidewalls, wherein one of said sidewalls includes an aperture dimensioned to receive a primate head therethrough.

14. The system according to claim 1, wherein
said laminar flow element includes a sheet with 0.25 inch perforations, and
each of said radial exhaust tubes includes downward facing apertures.

15. The system according to claim 13, wherein each of said tubes includes a sealed distal end and five 0.125 inch diameter lateral apertures.

16. The system according to claim 1, wherein said laminar flow element is a metal or plastic sheet having a plurality of perforations passing therethrough.

17. The system according to claim 1, wherein said aerosol delivery line includes a pipe passing through said inhalation chamber and said pipe having two slots running lengthwise and positioned 180° apart.

18. The system according to claim 1, wherein each radial exhaust tube includes a sealed distal end and a plurality of lateral holes.

19. A system comprising:
an inhalation exposure chamber having an ante-chamber;
an aerosol delivery line connected to said inhalation exposure chamber, said aerosol delivery line configured to produce a bi-directional and symmetrical presentation of aerosol to said inhalation exposure chamber;
a first laminar flow element;
a second laminar flow element; and
a radial exhaust having at least eight tubes extending radially out from a central hub, each of said tubes includes a plurality of downward facing apertures, and
wherein said radial exhaust and said laminar flow elements enable laminar flow of the aerosol through said inhalation exposure chamber; and
said first laminar flow element and said second laminar flow element defining the ante-chamber where complete and turbulent mixing of the aerosol occurs.

20. The system according to claim 19, further comprising a third laminar flow element spaced from said first and second laminar flow elements, and
wherein said first laminar flow element and said second laminar flow element are overlaid with each other.

* * * * *